(12) United States Patent
Chatelier et al.

(10) Patent No.: US 9,404,888 B2
(45) Date of Patent: Aug. 2, 2016

(54) SYSTEMS, DEVICES AND METHODS FOR IMPROVING ACCURACY OF BIOSENSORS USING FILL TIME

(71) Applicant: LifeScan, Inc., Milpitas, CA (US)

(72) Inventors: Ronald C. Chatelier, Bayswater (AU); Alastair M. Hodges, Bayswater (AU)

(73) Assignee: LifeScan, Inc., Milpitas, CA (US)

( * ) Notice: Subject to any disclaimer, the term of this patent is extended or adjusted under 35 U.S.C. 154(b) by 428 days.

(21) Appl. No.: 14/090,693

(22) Filed: Nov. 26, 2013

(65) Prior Publication Data

US 2014/0097097 A1    Apr. 10, 2014

Related U.S. Application Data

(63) Continuation of application No. 12/971,777, filed on Dec. 17, 2010, now Pat. No. 8,623,198, which is a continuation-in-part of application No. 12/649,594, filed on Dec. 30, 2009, now Pat. No. 8,101,065.

(51) Int. Cl.
*G01N 27/327* (2006.01)
*G01N 27/416* (2006.01)
*C12Q 1/00* (2006.01)

(52) U.S. Cl.
CPC .............. *G01N 27/416* (2013.01); *C12Q 1/006* (2013.01); *G01N 27/3273* (2013.01)

(58) Field of Classification Search
CPC ........................... G01N 27/26–27/401; G01N 27/404–27/4045; G01N 27/416–27/44
USPC .............. 204/403.01–403.15; 205/777.5, 792
See application file for complete search history.

(56) References Cited

U.S. PATENT DOCUMENTS

| 5,352,351 A | 10/1994 | White et al. ............. 204/403.04 |
| 5,385,846 A | 1/1995 | Kuhn et al. |
| 5,391,272 A | 2/1995 | O'Daly et al. ............. 205/777.5 |

(Continued)

FOREIGN PATENT DOCUMENTS

| CN | 1447117 A | 10/2003 |
| CN | 1558224 A | 12/2004 |

(Continued)

OTHER PUBLICATIONS

Japanese Office Action for JP 2010-284923; dated Feb. 25, 2014; 2 pages.

(Continued)

*Primary Examiner* — Bach Dinh
(74) *Attorney, Agent, or Firm* — Barclay Damon, LLP

(57) ABSTRACT

Methods for determining a concentration of an analyte in a sample, and the devices and systems used in conjunction with the same, are provided herein. In one exemplary embodiment of a method for determining a concentration of an analyte in a sample, the method includes detecting a presence of a sample in an electrochemical sensor including two electrodes. A fill time of the sample is determined with the two electrodes and a correction factor is calculated in view of at least the fill time. The method also includes reacting an analyte that causes a physical transformation of the analyte between the two electrodes. A concentration of the analyte can then be determined in view of the correction factor with the same two electrodes. Systems and devices that take advantage of the fill time to make analyte concentration determinations are also provided.

30 Claims, 13 Drawing Sheets

(56) References Cited

U.S. PATENT DOCUMENTS

| | | | |
|---|---|---|---|
| 5,582,697 A | 12/1996 | Ikeda et al. ............... 205/777.5 |
| 5,620,579 A | 4/1997 | Genshaw et al. |
| 5,653,863 A * | 8/1997 | Genshaw ............... C12Q 1/004 204/402 |
| 5,781,455 A | 7/1998 | Hyodo |
| 5,858,648 A | 1/1999 | Steel et al. |
| 5,942,102 A | 8/1999 | Hodges et al. |
| 6,174,420 B1 | 1/2001 | Hodges et al. |
| 6,193,873 B1 | 2/2001 | Ohara et al. |
| 6,241,862 B1 | 6/2001 | McAleer et al. |
| 6,284,125 B1 | 9/2001 | Hodges et al. |
| 6,379,513 B1 | 4/2002 | Chambers et al. |
| 6,413,410 B1 | 7/2002 | Hodges et al. |
| 6,424,847 B1 | 7/2002 | Mastrototaro et al. |
| 6,475,360 B1 | 11/2002 | Hodges et al. |
| 6,475,372 B1 | 11/2002 | Ohara et al. |
| 6,521,110 B1 | 2/2003 | Hodges et al. |
| 6,576,117 B1 | 6/2003 | Iketaki et al. |
| 6,599,407 B2 | 7/2003 | Taniike et al. |
| 6,632,349 B1 | 10/2003 | Hodges et al. |
| 6,638,415 B1 | 10/2003 | Hodges et al. |
| 6,676,995 B2 | 1/2004 | Dick et al. |
| 6,749,887 B1 | 6/2004 | Dick et al. |
| 6,780,645 B2 | 8/2004 | Hayter et al. |
| 6,797,150 B2 | 9/2004 | Kermani et al. |
| 6,830,934 B1 | 12/2004 | Harding et al. |
| 6,856,125 B2 | 2/2005 | Kermani |
| 6,869,411 B2 | 3/2005 | Langley et al. |
| 6,872,298 B2 | 3/2005 | Kermani |
| 6,895,263 B2 | 5/2005 | Shin et al. |
| 6,946,067 B2 | 9/2005 | Hodges et al. |
| 7,043,821 B2 | 5/2006 | Hodges |
| 7,045,054 B1 * | 5/2006 | Buck .................. A61B 5/14532 204/403.1 |
| 7,132,041 B2 | 11/2006 | Deng et al. |
| 7,195,704 B2 | 3/2007 | Kermani et al. |
| 7,199,594 B2 | 4/2007 | Kermani |
| 7,288,174 B2 | 10/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,431,820 B2 | 10/2008 | Hodges |
| 7,452,457 B2 | 11/2008 | Burke et al. |
| 7,488,601 B2 | 2/2009 | Burke et al. |
| 7,491,310 B2 | 2/2009 | Okuda et al. |
| 7,597,793 B2 | 10/2009 | Burke et al. |
| 7,749,371 B2 | 7/2010 | Guo et al. |
| 7,771,583 B2 | 8/2010 | Diamond et al. |
| 7,923,258 B2 | 4/2011 | Heller |
| 7,945,394 B2 | 5/2011 | Brown et al. |
| 8,101,065 B2 | 1/2012 | Chatelier et al. |
| 2002/0130043 A1 | 9/2002 | Hodges et al. ............ 204/403.1 |
| 2002/0150896 A1 | 10/2002 | Polonsky et al. |
| 2003/0155237 A1 | 8/2003 | Surridge et al. |
| 2003/0180814 A1 | 9/2003 | Hodges et al. |
| 2003/0201194 A1 | 10/2003 | Heller et al. |
| 2003/0203498 A1 | 10/2003 | Neel et al. |
| 2004/0079652 A1 | 4/2004 | Vreeke et al. |
| 2004/0120848 A1 | 6/2004 | Teodorczyk |
| 2004/0140209 A1 * | 7/2004 | Choi .................. G01N 33/5438 204/403.01 |
| 2004/0182703 A1 | 9/2004 | Bell et al. |
| 2004/0203137 A1 | 10/2004 | Hodges et al. |
| 2005/0000808 A1 | 1/2005 | Cui et al. ............... 204/403.14 |
| 2005/0004439 A1 | 1/2005 | Shin et al. |
| 2006/0108236 A1 | 5/2006 | Kaslelke et al. |
| 2006/0134713 A1 | 6/2006 | Rylatt et al. |
| 2006/0200017 A1 | 9/2006 | Monfre et al. |
| 2006/0217602 A1 | 9/2006 | Abul-Haj et al. |
| 2007/0000777 A1 | 1/2007 | Ho et al. |
| 2007/0024287 A1 | 2/2007 | Graves et al. |
| 2007/0034529 A1 | 2/2007 | Bard et al. |
| 2007/0074977 A1 | 4/2007 | Guo et al. |
| 2007/0131565 A1 | 6/2007 | Fujiwara et al. |
| 2007/0154951 A1 | 7/2007 | Kermanl |
| 2007/0227912 A1 | 10/2007 | Chatelier et al. |
| 2007/0231914 A1 | 10/2007 | Deng et al. |
| 2007/0235346 A1 | 10/2007 | Popovich et al. |
| 2008/0093230 A1 | 4/2008 | Diamond et al. |
| 2008/0098802 A1 | 5/2008 | Burke et al. |
| 2008/0105568 A1 | 5/2008 | Wu |
| 2008/0173552 A1 | 7/2008 | Wu et al. |
| 2008/0179197 A1 | 7/2008 | Wu |
| 2008/0199894 A1 | 8/2008 | Galasso |
| 2008/0214910 A1 | 9/2008 | Buck |
| 2008/0274447 A1 | 11/2008 | Mecklenburg |
| 2008/0293082 A1 | 11/2008 | Heller |
| 2009/0000959 A1 * | 1/2009 | Feldman .................. C12Q 1/54 205/777.5 |
| 2009/0005666 A1 | 1/2009 | Shin et al. |
| 2009/0017483 A1 | 1/2009 | Yamaoka et al. |
| 2009/0042306 A1 | 2/2009 | Reynolds et al. |
| 2009/0045076 A1 | 2/2009 | Burke et al. |
| 2009/0084687 A1 | 4/2009 | Chatelier et al. |
| 2009/0089010 A1 | 4/2009 | Burke et al. |
| 2009/0101523 A1 | 4/2009 | Deng |
| 2009/0112478 A1 | 4/2009 | Mueller, Jr. et al. |
| 2009/0157344 A1 | 6/2009 | Burke et al. |
| 2009/0292489 A1 | 11/2009 | Burke et al. |
| 2009/0301899 A1 | 12/2009 | Hodges et al. |
| 2010/0006452 A1 | 1/2010 | Hodges et al. |
| 2010/0089775 A1 | 4/2010 | Chen et al. |
| 2010/0173396 A1 | 7/2010 | Miller et al. |
| 2010/0270178 A1 | 10/2010 | Guo et al. |
| 2011/0073493 A1 | 3/2011 | Chateller et al. |
| 2011/0155584 A1 | 6/2011 | Chatelier et al. |
| 2011/0155585 A1 | 6/2011 | Chatelier et al. |

FOREIGN PATENT DOCUMENTS

| | | |
|---|---|---|
| CN | 1633596 A | 6/2005 |
| CN | 1975421 A | 6/2007 |
| CN | 101438143 A | 5/2009 |
| EP | 0735363 A1 | 10/1996 |
| EP | 0735363 A1 | 10/1996 |
| EP | 1 729 119 A1 | 12/2006 |
| EP | 1839571 A1 | 10/2007 |
| JP | 10-282037 | 10/1998 |
| JP | 2006-215034 | 8/2006 |
| TW | 200613724 A | 5/2006 |
| TW | 200946902 A1 | 11/2009 |
| WO | 03/069304 A2 | 8/2003 |
| WO | 2006/036833 A2 | 4/2006 |
| WO | WO 2006/119106 A1 | 11/2006 |
| WO | WO-2008150436 A1 | 12/2008 |
| WO | 2009/140343 A1 | 11/2009 |

OTHER PUBLICATIONS

Chinese Office Action for CN 201010621885.9; dated May 5, 2014; 8 pages.

European Office Action for EP 10252245.5; dated Aug. 20, 2014; 2 pages.

Taiwanese Search Report for TW 099139130; dated Nov. 26, 2014; 2 pages.

Chinese Office Action for CN 201010621885.9; dated: Dec. 31, 2014; 5 pages.

Japanese Office Action for JP 2014-096732; dated Jan. 20, 2015; 2 pages.

Japanese Office Action for JP 2014-096733; dated Jan. 20, 2015; 2 pages.

Canadian Office Action and Examination Search Report for CA 2,826,512; dated: Jan. 26, 2015; 3 pages.

European Office Action for EP 10 252 245.5; dated: May 22, 2015; 4 pages.

Singapore Search Report for SG 201308113-8; dated Jun. 16, 2015; 7 pages.

Canadian Office Action and Examination Search Report for CA 2,826,512; dated: Dec. 15, 2015; 4 pages.

Korean Office Action for KR Application No. 10-2010-0139601; mailing date Nov. 30, 2012; 10 pages.

(56) References Cited

OTHER PUBLICATIONS

Chinese Office Action for 201010621885.9; dated Oct. 22, 2013; 24 pages.
Australian Examination Report for AU 2012200759; dated Jul. 9, 2013; 4 pages.
Chinese Office Action and Search Report for CN 201010621885.9; dated Nov. 21, 2012; 6 pages.
Singapore Search Report/Written Opinion for SG 201009739-2; dated Apr. 2, 2013 and Apr. 3, 2013; 11 pages.
Australian Examiner's first report for Application No. 2010257395 dated Jun. 28, 2011 (2 Pages).
Australian Notice of Acceptance issued Oct. 27, 2011 for Application No. 2010257465 (3 Pages).
International Search Report and Written Opinion in PCT/IB2011/002472, dated Dec. 29, 2011 (12 Pages).
International Search Report and Written Opinion in PCT/US10/62629, dated Feb. 23, 2011.
Extended EP Search Report in EP 10252245.5, dated Jul. 7, 2011.
"WaveSense White Paper: Performance of the WaveSense KeyNote Blood Glucose Monitoring System Across 23 Lots of Test Strips", WaveSense, Mar. 2007, XP002640744, URL: http://www.wavesense.info/uploads/pdf/23lotstudyKeyNote.pdf.pdf.
Australian Notice of Acceptance issued Oct. 27, 2011 for Application No. 2010257465.
European Office Action for EP 10 252 245.5; dated: Jan. 11, 2016; 2 pages.

* cited by examiner

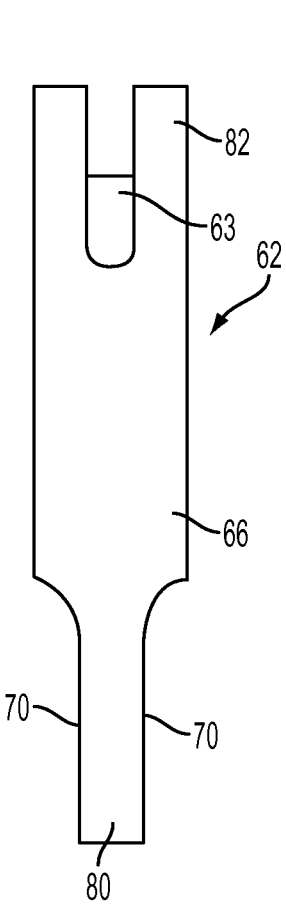
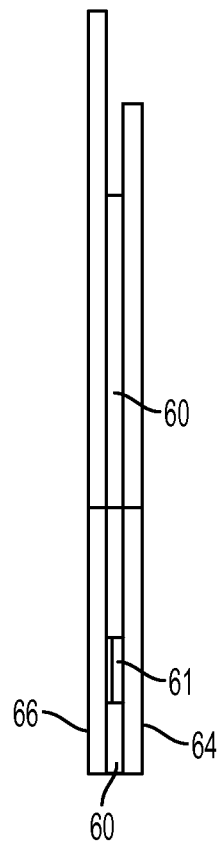
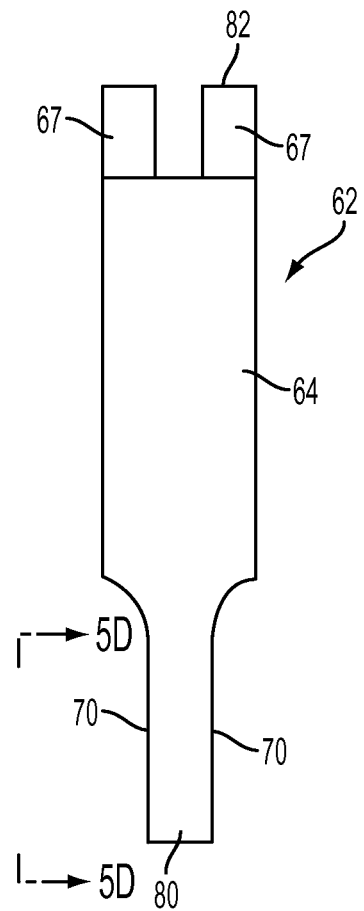
FIG. 5A   FIG. 5B   FIG. 5C
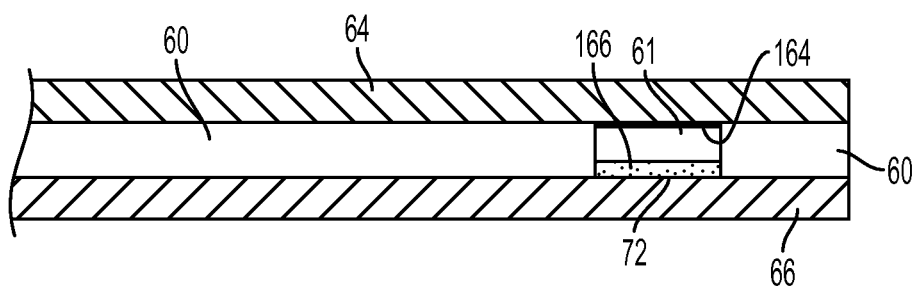
FIG. 5D

SYSTEMS, DEVICES AND METHODS FOR IMPROVING ACCURACY OF BIOSENSORS USING FILL TIME

CROSS REFERENCE TO RELATED APPLICATIONS

This application is a continuation application of U.S. patent application Ser. No. 12/971,777, entitled "Systems, Devices and Methods for Improving Accuracy of Biosensors Using Fill Tim" filed on Dec. 17, 2010, which is a continuation-in-part application of U.S. patent application Ser. No. 12/649,594, entitled "Systems, Devices and Methods for Improving Accuracy of Biosensors Using Fill Time" filed on Dec. 30, 2009, now issued U.S. Pat. No. 8,101,065 issued Jan. 24, 2012, each of these documents being incorporated by reference in their entirety.

FIELD

The present disclosure relates to determining a concentration of an analyte in a sample, and more particularly relates to making a more accurate determination of the concentration based on the fill time of the sample.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed. Some of these devices include electrochemical cells, electrochemical sensors, hemoglobin sensors, antioxidant sensors, biosensors, and immunosensors.

One characteristic of blood that can affect analyte detection is the haematocrit. Levels of haematocrit can be vastly different amongst various people. By way of non-limiting example, a person suffering from anemia may have a haematocrit level of approximately 20% while a neonate may have a haematocrit level of approximately 65%. Even samples taken from the same individual over a period of time can have different haematocrit levels. Further, because high haematocrit can also increase the viscosity of blood, and viscosity can in turn affect other parameters associated with analyte detection, accounting for the effect of haematocrit on a sample can be important in making accurate analyte concentration determinations.

One way in which varying levels of haematocrit in a blood sample have been accounted for is by separating the plasma from the blood and then recalculating the concentration of the antigen with respect to the adjusted plasma volume. Separation has been achieved, for example, by performing a centrifugation step. Other ways in which the varying levels of haematocrit in a blood sample have been accounted for include using an average haematocrit in a calculation or measuring a haematocrit in a separate step and then calculating the concentration of the antigen with respect to the plasma value. These methods, however, are believed to be undesirable, at least because they involve unwanted sample handling, take additional time, and/or lead to substantial errors in the final determinations. Further, temperatures in environments where samples are analyzed can also have a negative impact on the accuracy of analyte concentration determination.

SUMMARY

Applicants have recognized that it would be desirable to develop a way to obtain more accurate analyte concentration measurements that account for a wide spectrum of haematocrit levels and temperatures with little or none of the attendant issues noted previously. Accordingly, systems, devices, and methods are generally provided for determining a concentration of an analyte in a sample. In an exemplary embodiment of a method for determining a concentration of an analyte in a sample, the method includes detecting a presence of the sample in an electrochemical sensor. The electrochemical sensor can include, for example, two electrodes. The two electrodes can include, for example, an opposed faced orientation. In other embodiments, the two electrodes can include a facing orientation.

The method further includes determining a fill time of the sample with the two electrodes and calculating a correction factor in view of at least the fill time. The method also includes reacting an analyte to cause a physical transformation of the analyte between the two electrodes and determining the concentration of the analyte in view of the correction factor with the same two electrodes. For example, reacting of the analyte can generate an electroactive species that can be measured as a current by the two electrodes. In some embodiments, the fill time determination and the analyte concentration determination can both be determined using the same two electrodes.

In an exemplary embodiment of a method for measuring a corrected analyte concentration, the method includes detecting a presence of the sample in an electrochemical sensor. The electrochemical sensor can include, for example, two electrodes. The two electrodes can include, for example, an opposed faced orientation. In other embodiments, the two electrodes can include a facing orientation. The method further includes determining a fill time of the sample with the two electrodes. The method also includes reacting an analyte to cause a physical transformation of the analyte. The method further includes determining a first analyte concentration in the sample with the same two electrodes and calculating a corrected analyte concentration based on the first analyte concentration and the fill time. In some embodiments, the fill time determination and the analyte concentration determination can both be determined using the same two electrodes.

In one embodiment, the step of calculating the corrected analyte concentration can include calculating a correction factor based on the fill time. In such an embodiment, the corrected analyte concentration can be calculated based on the first analyte concentration and the correction factor. In an exemplary embodiment, the correction factor can be determined based on a series of threshold values. For example, the correction factor can be about zero when the fill time is less than a first fill time threshold. For another example, the correction factor can be calculated in view of the fill time when the fill time is greater than a first fill time threshold and less than a second fill time threshold. For yet another example, the correction factor can be a constant value when the fill time is greater than a second fill time threshold.

In some embodiments, the details of the step of calculating the corrected analyte concentration can depend on whether the first analyte concentration in the sample is less than or greater than a threshold value. For example, the step of calculating the corrected analyte concentration can include a sum of the correction factor and the first analyte concentration in the sample when the first analyte concentration in the sample is less than a threshold value. For another example, when the first analyte concentration in the sample is greater than a threshold value, the step of calculating the corrected analyte concentration can include dividing the correction factor by one hundred and adding one to give an intermediate term and multiplying the intermediate term by the first analyte concentration to give a fill time corrected analyte concentration.

In some embodiments of the above methods, the fill time of the sample can be determined by applying an electric potential between the two electrodes while the sample is introduced, measuring cell current as a function of time, and determining a current drop time based on cell current as a function of time. In such an embodiment, the current drop time can correspond to the fill time of the sample. In some embodiments, the step of determining current drop time can include calculating the maximum negative value of the change in measured cell current over time. In some embodiments, the step of determining current drop time can include calculating a difference between at least two current values where the difference is greater than a first predetermined threshold. In some embodiments, the step of determining current drop time can include calculating a difference between at least two current values where the difference is less than a second predetermined threshold. In some embodiments, the step of determining current drop time can include calculating a slope in the measured current as a function of time where the slope is greater than a third predetermined threshold. In some embodiments, the step of determining current drop time can include calculating a slope in the measured current as a function of time where the slope is less than a fourth predetermined threshold. In some embodiments, the step of determining current drop time can include calculating an inflection point in the measured current as a function of time. The measurement of cell current as a function of time can include, for example, performing current measurements approximately every 2 milliseconds and calculating and storing an average current based on the current measurements approximately every 10 milliseconds. In some embodiments, the method can further include determining a level of haematocrit in the sample in view of the fill time of the sample. As a result, the concentration of the antigen can be determined in view of the determined level of haematocrit.

In some embodiments of the above methods, detecting the presence of a sample can include applying an electric potential between the two electrodes, and measuring a change in current values that is greater than a fifth predetermined threshold. In some embodiments, detecting the presence of a sample can include applying an electric potential between the two electrodes, and measuring a change in current values that is less than a sixth predetermined threshold. In some embodiments detecting the presence of a sample can include applying a generally constant current between the two electrodes and measuring a change in an electric potential that is greater than a seventh predetermined threshold. In some embodiments, detecting the presence of a sample can include applying a generally constant current between the two electrodes and measuring a change in an electric potential that is less than an eighth predetermined threshold. In some embodiments, detecting the presence of the sample can be performed by a microprocessor of an analyte measuring machine.

The electrochemical cell can include a glucose sensor. In another embodiment the electrochemical cell can include an immunosensor. In such an embodiment, the analyte for which the concentration is being analyzed can include C-reactive protein. The analyzed sample can include blood. In one embodiment the blood can include whole blood. The analyte for which the concentration is being analyzed can include glucose.

In an exemplary embodiment of a method for measuring a corrected analyte concentration, the method includes detecting a presence of the sample in an electrochemical sensor. The electrochemical sensor can include, for example, two electrodes. The method further includes determining a fill time of the sample with the two electrodes. The method also includes reacting an analyte that causes a physical transformation of the analyte. The method further includes determining a first analyte concentration in the sample with the same two electrodes and calculating a corrected analyte concentration based on the first analyte concentration and the fill time. In some embodiments, the fill time determination and the analyte concentration determination can both be determined using the same two electrodes.

In one embodiment, the step of calculating the corrected analyte concentration can include calculating a correction factor based on the fill time. In such an embodiment, the corrected analyte concentration can be calculated based on the first analyte concentration and the correction factor. In an exemplary embodiment, the correction factor can be determined based on a series of threshold values. For example, the correction factor can be about zero when the fill time is less than a first fill time threshold. For another example, the correction factor can be calculated in view of the fill time when the fill time is greater than a first fill time threshold and less than a second fill time threshold. For yet another example, the correction factor can be a constant value when the fill time is greater than a second fill time threshold.

In some embodiments, the details of the step of calculating the corrected analyte concentration can depend on whether the first analyte concentration in the sample is less than or greater than a threshold value. For example, the step of calculating the corrected analyte concentration can include a sum of the correction factor and the first analyte concentration in the sample when the first analyte concentration in the sample is less than a threshold value. For another example, when the first analyte concentration in the sample is greater than a threshold value, the step of calculating the corrected analyte concentration can include dividing the correction factor by one hundred and adding one to give an intermediate term and multiplying the intermediate term by the first analyte concentration to give a fill time corrected analyte concentration.

In one exemplary embodiment of an electrochemical system, the system includes an electrochemical sensor including electrical contacts configured to mate with a test meter. The electrochemical sensor includes a first electrode and a second electrode in a spaced apart relationship and a reagent. The first and second electrodes can include, for example, an opposed faced orientation. In other embodiments, the first and second electrodes can include a facing orientation. The system also includes a test meter including a processor configured to receive current data from the test strip upon application of voltages to the test strip, and further configured to determine a corrected analyte concentration based on a calculated analyte concentration and a measured fill time with the same two electrodes. The system can also include a heating element configured to heat at least a portion of the electrochemical sensor. In some embodiments, the test meter can include data includes data storage that contains an analyte concentration threshold, a first fill time threshold, and a second fill time threshold. In some embodiments, at least one of the electrochemical sensor, the test meter, and the processor are configured to measure a temperature of the sample.

In one embodiment, the electrochemical cell can be a glucose sensor. In another embodiment, the electrochemical cell can be an immunosensor. The immunosensor can include a first liquid reagent, a second liquid reagent, and magnetic beads conjugated to an antigen. In one embodiment the first liquid reagent can include an antibody conjugated to an enzyme in a buffer. The first liquid reagent can be striped on the lower electrode and can be dried. The second liquid reagent can include ferricyanide, a substrate for the enzyme, and a second mediator in a dilute acid solution. The second liquid reagent can be striped on the lower electrode and can be dried. The magnetic beads, on the other hand, can be striped on the upper electrode and dried.

The immunosensor can also include a plurality of chambers, a separator, a vent, and one or more sealing components. The separator can be disposed between the lower and the upper electrodes. The plurality of chambers can include a reaction chamber, a detection chamber, and a fill chamber. The reaction chamber can be formed in the separator and can have the first reagent and the magnetic beads conjugated to the antigen disposed therein. The detection chamber can also be formed in the separator and can have the second reagent disposed therein. The fill chamber can be formed at least partially in the separator and one of the lower and upper electrodes, can be spaced a distance apart from the detection chamber, and can overlap at least a portion of the reaction chamber. The vent can be formed at least partially in each of the separator, the lower electrode, and the upper electrode, can be spaced a distance apart from the reaction chamber, and can overlap at least a portion of the detection chamber. In one embodiment the one or more sealing components can be a first sealing component and a second sealing component. The first sealing component can have an incorporated anticoagulant coupled to one of the lower and upper electrodes, can be disposed over the vent, and can be configured to both form a wall of the fill chamber and seal the vent. The second sealing component can be coupled to the other of the lower and upper electrodes, can be disposed over the vent, and can be configured to seal the vent. In one embodiment the first sealing component is a hydrophilic adhesive tape. At least one of the control unit, the immunosensor, and the meter can include a configuration to measure a temperature of the sample. The analyte for which the system calculates the concentration can include C-reactive protein. The sample introduced into the electrochemical cell can include blood. In one embodiment the blood can include whole blood.

The electrochemical sensor can also be a number of other analyzing devices, including, by way of non-limiting example, electrochemical cells, glucose sensors, glucose meters, hemoglobin sensors, antioxidant sensors, biosensors, and immunosensors. In one embodiment the electrochemical sensor is a glucose sensor. The glucose sensor can include an electrochemical cell having a working electrode and a counter or counter/reference electrode. The working electrode and the counter or counter/reference electrode can be spaced apart by approximately 500 micrometers or less. In one embodiment a spacing between the electrodes is in the range of about 80 micrometers to about 200 micrometers. The spacing can be determined in order to achieve a desired result, for example, substantially achieving a steady state current in a desirable time. In one embodiment a spacing between the electrodes is selected such that the reaction products from a counter electrode arrive at a working electrode.

The working and counter or counter/reference electrode can have a variety of configurations. For example, the electrodes can be facing each other, they can be substantially opposed to each other, or they can have a side-by-side configuration in which the electrodes are positioned approximately in the same plane. The electrodes can have substantially the same corresponding area. The electrodes can also be planar. In one embodiment the electrochemical cell includes a working electrode, a counter electrode, and a separate reference electrode. In another embodiment the electrochemical cell can have two electrode pairs. The electrode pairs can include any combination of working, counter, counter/reference, and separate reference electrodes, but in one exemplary embodiment each pair includes a working electrode and a counter or counter/reference electrode. In still another embodiment the electrochemical cell can have an effective cell volume of about 1.5 microliters or less. The electrochemical cell can be hollow.

A potential can be applied to the electrodes of the cells by a number of different mechanisms, including, by way of non-limiting example, a meter. The magnitude of the potential can depend on a number of different factors, including, by way of non-limiting example, the desired reaction of the sample within the cell. In one embodiment the magnitude of the potential can be selected such that electro-oxidation of a reduced form or electro-reduction of an oxidized form of a sample is substantially diffusion controlled.

Samples can enter the cell by way of capillary action. A control unit can be used to determine a fill time of the sample entering the cell. In one embodiment the control unit can include a current flow detector configured to measure cell current as a function of time to determine a current drop corresponding to the fill time of the sample. At least one of the control unit, the electrochemical cell, and the meter can be configured to measure a temperature of the sample, or alternatively a temperature of the ambient air inside of the meter or proximate to the electrochemical sensor attached to the meter.

One exemplary embodiment of a method for measuring an antigen in a blood sample can include providing an immunosensor having two electrodes and a meter connected to the electrochemical cell so that the meter applies a potential between the two electrodes of the immunosensor. The method can further include introducing a blood sample including an antigen into the immunosensor, applying an electric potential between the two electrodes, calculating a fill time of the blood sample, and determining a concentration of the antigen in view of the fill time. The immunosensor can further include a reaction chamber and a detection chamber formed in a separator disposed between the two electrodes, a fill chamber at least partially formed in the separator and one of the two electrodes, and a vent at least partially formed in the separator and the two electrodes. The fill chamber can be spaced a distance apart from the detection chamber and can overlap at least a portion of the reaction chamber. The vent can be spaced a distance apart from the reaction chamber and can overlap at least a portion of the detection chamber. The antigen of the blood sample can be C-reactive protein. The method can further include measuring a temperature of the blood sample. As a result, a concentration of the antigen can be calculated in view of fill time.

The method for measuring a blood sample can further include providing an antibody-enzyme conjugate in a first buffer and magnetic beads linked to an antigen in a second buffer in the reaction chamber. Ferricyanide, glucose, and a mediator in a dilute acid can be provided in the detection chamber. A first seal can be provided over a first side of the vent that forms a wall of the fill chamber and a second seal can be provided over a second side of the vent. At least a portion of the blood sample that is introduced into the immunosensor moves from the fill chamber to the reaction chamber when it is introduced into the immunosensor.

The method can further include opening the vent after a pre-determined time by piercing at least one of the seals. Piercing at least one of the seals allows portions of the blood sample containing the antibody-enzyme conjugate that are not bound to the magnetic beads to move to the detection chamber. Still further, the method can include catalyzing oxidation of the glucose in the detection chamber, which can result in the formation of ferrocyanide. A current can be electrochemically detected from the ferrocyanide, and a concentration of the antigen in the blood sample can be calculated in view of the signal detected.

BRIEF DESCRIPTION OF DRAWINGS

This invention will be more fully understood from the following detailed description taken in conjunction with the accompanying drawings, in which:

FIG. 5A illustrates a bottom plan view of one embodiment of a test strip disclosed herein;

FIG. 5B illustrates a side plan view of the test strip of FIG. 5A;

FIG. 5C illustrates a top plan view of the test strip of FIG. 5B;

FIG. 5D is a partial side view of a proximal portion of the test strip of FIG. 5C;

DETAILED DESCRIPTION

Figure 1:
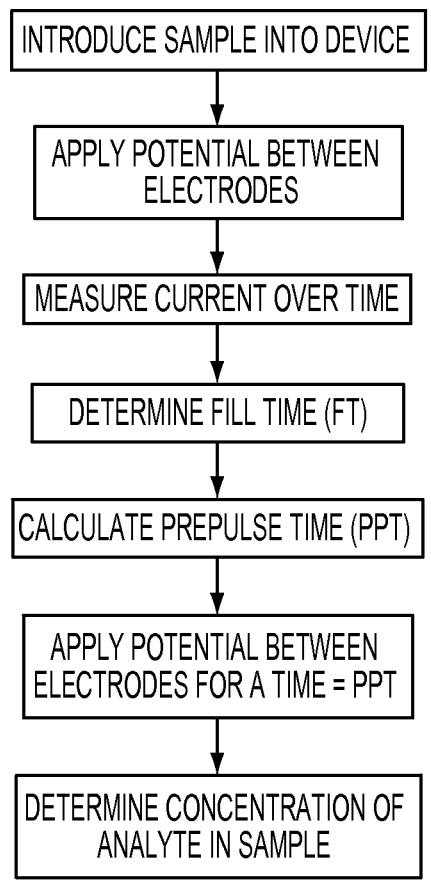
FIG. 1 illustrates a flow chart of an exemplary method of a method of determining the concentration of an analyte in a sample in accordance with the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The presently disclosed systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system based on a thin-layer cell design with opposing electrodes and tri-pulse electrochemical detection that is fast (e.g., about 5 second or less analysis time), requires a small sample (e.g., about 0.4 µL or less), and can provide improved reliability and accuracy of blood glucose measurements. In the reaction cell to assay analyte, glucose in the sample can be oxidized to gluconolactone using glucose dehydrogenase and an electrochemically active mediator can be used to shuttle electrons from the enzyme to a palladium working electrode. More particularly, a reagent layer coating at least one of the electrodes in the reaction cell can include glucose dehydrogenase (GDH) based on pyrroloquinoline quinone (PQQ) co-factor and ferricyanide. In another embodiment, the enzyme GDH based on the PQQ co-factor may be replaced with the enzyme GDH based on the flavin adenine dinucleotide (FAD) co-factor. When blood or control solution is dosed into the reaction chamber, glucose is oxidized by GDH(ox) and in the process converts GDH(ox) to GDH(red), as shown in the chemical transformation T.1 below. Note that GDH(ox) refers to the oxidized state of GDH, and GDH (red) refers to the reduced state of GDH.

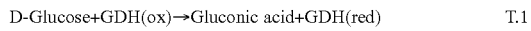

A potentiostat can be utilized to apply a tri-pulse potential waveform to the working and counter electrodes, resulting in test current transients used to calculate the glucose concentration. Further, additional information gained from the test current transients may be used to discriminate between sample matrices and correct for variability in blood samples due to hematocrit, temperature variation, electrochemically active components, and identify possible system errors.

The subject methods can be used, in principle, with any type of electrochemical cell having spaced apart first and second electrodes and a reagent layer. For example, an electrochemical cell can be in the form of a test strip. In one aspect, the test strip may include two opposing electrodes separated by a thin spacer for defining a sample-receiving chamber or zone in which a reagent layer is located. Applicants note that other types of test strips, including, for example, test strips with co-planar electrodes may also be used with the methods described herein.

The methods for determining a concentration of an analyte in a sample disclosed herein can be used with any sample analyzing device and/or system. The devices typically include at least one working electrode and one counter electrode between which an electric potential can be applied. The sample analyzing device can generally be associated with a component for applying the electric potential between the electrodes, such as a meter. Applicants note that a variety of test meters can be used with the systems and methods described herein. However, in one embodiment, the test meter includes at least a processor, which may include one or more control units configured for performing calculations capable of calculating a correction factor in view of at least one measured or calculated parameter as well as configured for data sorting and/or storage. The microprocessor can be in the form of a mixed signal microprocessor (MSP) such as, for example, the Texas Instruments MSP 430. The TI-MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit.

The sample analyzing device can also be associated with one or more components that are capable of measuring a fill time of a sample when it is introduced to the device. Such components can also be capable of calculating a concentration of an analyte in the sample in view of the fill time. Such components are generally referred to herein as control units. Further, the terms analyte, antigen, and antibodies are used interchangeably within, and thus, use of one term is equally applicable to all three terms, unless otherwise indicated or reasonably known by one skilled in the art.

In one exemplary embodiment of a method for determining a concentration of an analyte in a sample, a sample is introduced into an electrochemical cell of a sample analyzing device that has a working electrode and a counter electrode. An electric potential can be applied between the working and counter electrodes of the electrochemical cell and a fill time of the sample into, for example, a capillary space of the electrochemical cell, can be determined. A prepulse time can be calculated in view of at least the fill time of the sample and an electric potential can be applied between the working electrode and the counter electrode for a length of time equal to the prepulse time. A concentration of the analyte in the sample can then be determined. By calculating the prepulse time in view of the fill time, more accurate results can be achieved for analyte concentration. For example, errors, such as those that can result from varying haematocrit levels across samples, can be accounted for, thereby leading to more accurate determinations of the concentrations of the analytes in the samples. Methods can also account for the effects of temperature, as discussed in greater detail below. In an alternative embodiment for detecting a concentration of an analyte in a sample, errors are corrected for based on a determined initial fill velocity rather than a determined fill time. One example of such a method is disclosed in U.S. patent application Ser. No. 12/649,509 entitled "Systems, Devices and Methods for Measuring Whole Blood Haematocrit Based on Initial Fill Velocity," of Ronald C. Chatelier, Dennis Rylatt, Linda Raineri, and Alastair M. Hodges, published as U.S. Patent Application Publication No. 2011/0155584 A1 and filed on Dec. 30, 2009, the contents of which is hereby incorporated by reference in its entirety.

In an alternative embodiment, an estimate of a level of haematocrit level can be determined. In some embodiments, the estimate of a level of haematocrit can be determined without reference to an associated analyte concentration. As a result, assessments related to conditions such as anemia can be made. In such a system, only a level of haematocrit is measured without making other concentration determinations. Determining a level of haematocrit based on the disclosed teachings can allow determinations to be made quickly and accurately, often in less than a second. For example, haematocrit levels of a drop of blood can be determined in less than a second merely by dropping the blood onto a sensor strip of a sample analyzing device. Once the blood is disposed on the strip, a digital readout of the haematocrit level can be provided almost instantaneously.

A fill time can be used in a variety of ways to improve a determination of a concentration of an analyte. For example, the fill time of the sample can be used to calculate a prepulse time. By adjusting the prepulse time in view of the fill time, longer reaction times can be provided for samples which take a longer time to fill the sensor. For example, if the sample includes whole blood, then haematocrit level can be a factor in the fill time of the sample. Adjusting the prepulse time in view of the fill time can thus allow for more accurate concentrations to be determined over a range of haematocrit levels. In some embodiments, the haematocrit level can be linked to the fill time, e.g., an estimate of the haematocrit level can be determined in view of the fill time. In such an instance, the haematocrit levels can be accounted for in the determination of the analyte concentration in order to provide more accurate analyte concentration determinations.

In one exemplary embodiment, the steps illustrated in FIG. 1 can be used to determine the concentration of an analyte in a sample. As shown, a sample is first introduced into the device. Any type of sample analyzing devices can be used in conjunction with at least some of the systems and methods disclosed herein. These devices can include, by way of non-limiting example, electrochemical cells, electrochemical sensors, glucose sensors, glucose meters, hemoglobin sensors, antioxidant sensors, biosensors, and immunosensors. One exemplary embodiment of a sample analyzing device is an electrochemical sensor. The electrochemical sensor can include at least two electrodes. The at least two electrodes can be configured in any way, for example, the electrodes can be on the same plane or on different planes. A sample can be introduced into the electrochemical cell.

In one embodiment, the introduction of a sample may be detected by an automatic technique in which the meter monitors a change in voltage, current, or capacitance, a change which indicates that sample has been dosed into the sample reaction chamber. Alternatively, the physiological sample may be detected by a manual technique in which the user visually observes the filling of the sample reaction chamber and initiates the test by pressing a button. In another embodiment, an optical detector in the meter can sense the dosing of the sample. The time taken by the sample to fill the reaction chamber can likewise be measured by any number of similar techniques. In one embodiment, the electrodes can be configured such that when a sample is introduced into the sensor, the second electrode is contacted prior to or simultaneous with the first electrode as the sample fills the sensor. However, as the sample fills the sensor, the first electrode is limiting in the current it can sustain relative to the voltage applied to the second electrode. The first electrode can therefore limit the current flowing in the electrochemical sensor. Prior to, simultaneous with, or immediately after the sample contacts the first electrode, a potential can be applied between the electrodes such that when the first and second electrodes are bridged by the sample liquid a current flows between them. In one embodiment of the methods disclosed herein, the current versus time response during the sensor filling can be used to determine the point at which the sensor is adequately filled. For example, adequate filling can mean that sufficient liquid has filled the sensor to entirely cover at least the first electrode. In some embodiments, the current versus time response can be a discontinuity in the rate of change of current with time, such as an increased drop in current or a decreased rate of increase. One example of the above methods is disclosed in U.S. patent application Ser. No. 12/885,830 of Kranendonk et al., entitled "Apparatus and Method for Improved Measurements of a Monitoring Device," published as U.S. Patent Application Publication No. 2012/0067741 A1 and filed on Sep. 20, 2010, the contents of which is hereby incorporated by reference in its entirety.

In one embodiment of the methods disclosed herein, a potential of between about +10 mV to about +30 mV can be applied between the first and second electrodes of an electrochemical cell for a period of time, e.g., about 1000 ms, as a sample introduced into the device fills the cell. In one exemplary embodiment, a potential of about +20 mV can be applied between the first and second electrodes as a sample introduced into the device fills the cell. The current flowing between the electrodes can be measured at predetermined intervals during this time. For example, the current can be measured every 2 milliseconds ("ms") and the average current can be stored every 10 ms. The current data can then be analyzed, by a control unit, for example. In some embodiments, the control unit can include a microprocessor. The analysis of the current data measured over the approximately 1000 ms, during which the sample fills the device, can include a determination of the latest time at which the current decreases by a predetermined amount. This time can be used as the fill time (FT) of the sample. For example, in one embodiment, the latest time at which the current decreases by more than 0.4 micro-Ampere ("µA") over a 40 ms interval can be used to determine the time at which the sample has filled the cell.

In some embodiments, the step of determining current drop time can include calculating a difference between in at least two current values where the difference is greater than or less than a predetermined threshold value. Various predetermined threshold values can be employed. For example, when the area of the working electrode is about 4.2 square millimetres and hematocrits as high as about 75% are being assayed, the predetermined threshold value can be in the range of about 0.4 microamperes over about a 40 ms time period. In other exemplary embodiment, when the area of the working electrode is about 4.2 square millimetres and hematocrits as high as about 60% are being assayed, the predetermined threshold value can be in the range of about 0.7 microamperes to about 0.9 microamperes over about a 50 ms time period. In some embodiments, the step of determining current drop time can include calculating an inflection point in the measured current as a function of time.

In some embodiments, detecting the presence of a sample can include applying an electric potential between the two electrodes, and measuring a change in current values that is greater than or less than a predetermined threshold value. Various predetermined threshold values can be employed. For example, when the area of the working electrode is about 4.2 square millimeters, the predetermined threshold value can be in the range of about 3 microamperes. In other embodiments, detecting the presence of a sample can include applying a generally constant current between the two electrodes, and measuring a change in an electric potential that is greater than or less than a predetermined threshold. For example, the predetermined threshold value can be in the range of about 200 mV. In other exemplary embodiment, the threshold value can be about 400 mV.

After the sample has filled the cell, a first electric potential, having a first polarity, can be applied between a first and second electrode and a resulting current measured as a function of time. This first electric potential can be referred to, for example, as a prepulse. In some embodiments, the length of time that a prepulse can be applied can be about 5 seconds. In other embodiments, the fill time (FT) of the sample, which can be determined using any of the techniques discussed above, can be used to calculate the length of time that a prepulse can be applied. This time period can be referred to, for example, as a prepulse time (PPT). For example, the calculation of prepulse time can allow for longer prepulse times for samples that take longer to fill the sensor. In one embodiment, the prepulse time can be set according to the following exemplary parameters. For example, the prepulse time can be calculated as:

$$PPT(ms) = 3000 + (FT - 300) \times 9.3$$

For purposes of this calculation, for fill times less than 300 ms, the fill time can be set to 300 ms. This calculation allows the prepulse time (PPT) to be adjusted to allow for longer reaction times for samples that take more than a predetermined amount of time, e.g., about 300 ms, to fill the sensor. For purposes of simplifying calculation and to place boundaries on the total test time a maximum prepulse time can be set if the fill time is longer than a predetermined length of time. For example, in one embodiment, if the fill time is greater than about 500 ms, e.g., about 515 ms, the prepulse time (PPT) can be set equal to 5000 ms. Thus, in this exemplary embodiment, the minimum PPT (for fill times less than about 300 ms) is 3000 ms and the maximum PPT (for fill times greater than about 500 ms, e.g., about 515 ms) is about 5000 ms. In other embodiments, the calculation of prepulse time can be adjusted so as to take into account other properties and requirements of a particular sample or analyte. For example, the variables and constants in the equation shown above for calculation of prepulse time can be adjusted so as to provide alternate maximum and minimum prepulse times, or combinations thereof.

Once the prepulse time has been determined, a potential can be applied between the electrodes of the cell for a time equal to the prepulse time (PPT) and a resulting current measured as a function of time. At least a portion of the data (current as a function of time) provides a first time-current transient. The first electrical potential can be sufficiently negative with respect to the second electrode such that second electrode functions as the working electrode in which a limiting oxidation current is measured. After the first time interval has elapsed, a second electric potential can be applied between the first and second electrodes for a second time interval. The second electrical potential causes a current that is measured as a function of time to produce a second time-current transient. In one embodiment, the second potential has a second polarity, which is opposite to the first polarity. For example, the second potential can be sufficiently positive with respect to second electrode such that first electrode functions as the working electrode in which a limiting oxidation current is measured. In one exemplary embodiment, the first electrical potential and second electrical potential can range from about −0.6 V to about +0.6 V. The time interval of the time-current transients can, in one embodiment, can be in the range of about 1 second to 10 seconds, and preferably in the range of about 1 to 5 seconds. In another embodiment, a sum of the first time interval and the second time interval is less than about 5 seconds. It should also be noted that the first time interval does not have to be the same as the second time interval. In one embodiment, the second electric potential is applied immediately following the application of the first electric potential. In an alternative embodiment, a delay or open circuit potential is introduced in between the first electric potential and the second electric potential. In another alternative embodiment, a delay is introduced after physiological sample is detected in the sample reaction chamber, but before the application of the first electric potential. The delay can be in the range of about 0.01 and about 3 seconds, preferably from about 0.05 to about 1 second and most preferably from about 0.5 to about 0.9 seconds.

In one exemplary embodiment, a first test potential $E_1$ can be applied between the electrodes for a first test potential time $T_1$, e.g., PPT milliseconds. For example, a potential of +300 mV can be applied. After the first test potential time $T_1$, e.g., PPT milliseconds, has elapsed, a second test potential $E_2$ can be applied between the electrodes for a second test potential time interval $T_2$, e.g., −300 mV for 1000 ms. During $T_1$ and $T_2$, the cell current as a function of time can be measured, herein called a time current transient or a current transient and referred to as $i_a(t)$, during first test potential time interval $T_1$, and as $i_b(t)$ during the second test potential time interval $T_2$. For example, the current as a function of time can be measured every 10 ms with the average current stored every 50 ms. At least a portion of the data from the first and second potentials (current as a function of time) can provide first and second time-current transients. The concentration of an analyte in the sample can then be determined from the current data using any number of algorithms.

Examples of algorithms for determining analyte concentration can be found at least in U.S. Pat. No. 8,163,162 of Chatelier et al., entitled "Methods And Apparatus For Analyzing A Sample In The Presence Of Interferents," and filed on Mar. 31, 2006, the contents of which is hereby incorporated by reference in its entirety. In one exemplary embodiment, the current data can be analyzed using a "calibration-free, corner-corrected algorithm" similar to those disclosed in the aforementioned patent application. In one embodiment, an analyte concentration can be calculated using the algorithm as shown in Equation (Eq.) 1.

$$G = \left(\frac{i_r}{i_l}\right)^P \{ai_2 - zgr\} \qquad \text{Eq. 1}$$

In Eq. 1, G is the analyte concentration, the terms $i_l$, $i_r$, and $i_2$ are current values and the terms p, zgr, and a are empirically derived calibration constants.

In one embodiment of the invention, p may range from about 0.2 to about 4, and preferably from about 0.1 to about 1. The calibration factor a can be used to account for possible variations in the dimensions of the electrochemical cell. Variations in the dimensions of the electrochemical cell can cause a proportional shift in the magnitude of the measured current. Under certain circumstances, manufacturing processes can cause the electrode area to vary from one lot of test strips to another lot of test strips. Calculating a calibration factor a for each lot of test strips helps to compensate for variations in electrode area and the height of the cell. The term a can be calculated during the calibration process of a test strip lot.

A calibration factor zgr is used to account for variations in the background. A presence of an oxidizable species within the reagent layer of the cell before the addition of a sample may contribute to a background signal. For example, if the reagent layer were to contain a small amount of ferrocyanide (e.g., reduced mediator) before the sample was added to the test strip, then there would be an increase in the measured test current which would not be ascribed to the analyte concentration. Because this would cause a constant bias in the overall measured test current for a particular lot of test strips, this bias can be corrected for using the calibration factor Z. Similar to the terms p and a, Z can also be calculated during the calibration process. Exemplary methods for calibrating strip lots are described in U.S. Pat. No. 6,780,645 which is hereby incorporated by reference in its entirety.

In one exemplary embodiment, p can be 0.51, a can be 0.2, and zgr can be 5. While the method disclosed herein is described with the use of calibration factors, p, a, and zgr, one skilled in the art will appreciate that their use is not required. For example, in one embodiment, glucose concentration could be calculated without p, a, and/or Z (in Eq. 1 p and/or a could be set equal to one and zgr could be set equal to zero). A derivation of Eq. 1 can be found in U.S. Pat. No. 7,749,371, which was filed on Sep. 30, 2005 and entitled "Method and Apparatus for Rapid Electrochemical Analysis," which is hereby incorporated by reference in its entirety.

Current value $i_r$ can be calculated from the second current transient and current value $i_l$ can be calculated from the first current transient. All current values (e.g. $i_r$, $i_l$, and $i_2$) stated in Eq. 1 and in subsequent equations can use the absolute value of the current. Current values $i_r$, $i_l$, can be, in some embodiments, an integral of current values over a time interval of a current transient, a summation of current values over a time interval of a current transient, or an average or single current value of a current transient multiplied by a time interval of the current transient. For the summation of current values, a range of consecutive current measurement can be summed together from only two current values or to all of the current values. Current value $i_2$ can be calculated as discussed below.

For example, where the first time interval is 5 seconds long, $i_l$ may be the average current from 1.4 to 4 seconds of a 5 second long period and $i_r$ may be the average current from 4.4 to 5 seconds of a 5 second long period, as shown in Eq. 2a and 3a, below.

$$i_r = \sum_{t=4.4}^{5} i(t) \qquad \text{Eq. 2a}$$

$$i_l = \sum_{t=1.4}^{4} i(t) \qquad \text{Eq. 3a}$$

In another example, where the first interval is 5 seconds long $i_l$ may be the sum of currents from 3.9 to 4 seconds of a 5 second long period and $i_r$ may be the sum of currents from 4.25 to 5 seconds of a 5 second long period, as shown in Eq. 2b and 3b, below.

$$i_r = \sum_{t=4.25}^{5} i(t) \qquad \text{Eq. 2b}$$

$$i_l = \sum_{t=3.9}^{4} i(t) \qquad \text{Eq. 3b}$$

A magnitude of current for the first current transient can be described as a function of time by Eq. 4.

$$i_a(t) = i_{ss}\left\{1 + 2\sum_{n=1}^{\infty} \exp\left(\frac{-4\pi^2 n^2 Dt}{L^2}\right)\right\} \qquad \text{Eq. 4}$$

The term $i_{ss}$ is the steady-state current following the application of first test potential $E_1$, D is the diffusion coefficient of the mediator, L is the thickness of the spacer. It should be noted that in Eq. 4, t refers to the time elapsed after first test potential $E_1$ was applied. A magnitude of current for the second current transient can be described as a function of time by Eq. 5.

$$i_b(t) = i_{ss}\left\{1 + 4\sum_{n=1}^{\infty} \exp\left(\frac{-4\pi^2 n^2 Dt}{L^2}\right)\right\} \qquad \text{Eq. 5}$$

There is a factor of two difference for the exponential term in Eq. 5 as compared to the exponential term in Eq. 4 because the second current transient is generated from the second test potential $E_2$, which was opposite in polarity to the first test potential $E_1$, and was applied immediately after the first test potential $E_1$. It should be noted that in Eq. 5, t refers to the time elapsed after second test potential $E_2$ was applied.

A peak current for first test potential time interval $T_1$ can be denoted as $i_{pa}$ and a peak current for second test potential time interval $T_2$ can be denoted as $i_{pb}$. If both first peak current $i_{pa}$ and second peak current $i_{pb}$ were measured at the same short time after the application of first test potential $E_1$ and second test potential $E_2$ respectively, for example 0.1 seconds, Eq. 4 can be subtracted from Eq. 5 to yield Eq. 6.

$$i_{pb} - 2i_{pa} = -i_{ss} \qquad \text{Eq. 6}$$

Because it has been determined that $i_{pa}$ is controlled mainly by interferents, $i_{pb}$ can be used with $i_{pa}$ together to determine a correction factor. For example, as shown below $i_{pb}$ can be used with $i_{pa}$ in a mathematical function to determine a corrected current which is proportional to glucose and less sensitive to interferents.

Eq. 7 was derived to calculate a current $i_4$ which is proportional to glucose and has a relative fraction of current removed that is ascribed to interferents.

$$i_2 = i_r\left\{\frac{i_{pb} - 2i_{pa} + i_{ss}}{i_{pb} + i_{ss}}\right\} \qquad \text{Eq. 7}$$

The term $i_{ss}$ was added to both the numerator and denominator to allow the numerator to approach zero when no glucose is present. The term $i_{ss}$ may be estimated using Equation 8A, for currents at times greater than a minimum time, where a suitable minimum time can be estimated from Equation 8B.

$$i(t) = i_{ss}\left\{1 + 4\exp\left(\frac{-4\pi^2 Dt}{L^2}\right)\right\} \qquad \text{Eq. 8A}$$

$$t_{min} = \frac{-L^2 \ln 0.01}{12\pi^2 D} \qquad \text{Eq. 8B}$$

in which, $i_{ss}$ is the steady-state current following application of the second electric potential; i is the measured current which is a function of time; D is the diffusion coefficient of the redox-active molecule, where this coefficient may be determined from Fick's first law, i.e. $J(x,t)=-DdC(x,t)/dx$; L is the spacer thickness; and t is the time for the application of the second electric potential where t=0 for the beginning of the second time interval.

In one exemplary embodiment, the current value, $i_2$, can be calculated according to Eq. 9.

$$i_2 = i_r\left(\frac{i(4.1) - 2i(1.1) + i_{ss}}{i(4.1) + i_{ss}}\right) \qquad \text{Eq. 9}$$

Thus, Eq. 1 can enable accurate measurements of analyte concentration in the presence of interferents.

As discussed above, an estimate of a level of haematocrit can be determined without reference to an associated analyte concentration. For example, haematocrit levels of a drop of blood can be determined from current values and an analyte concentration. In one exemplary embodiments, an estimate of the haematocrit (H) can be derived from Eq. 10.

$$H = -162.5 \log(i_r) + 119.1 \log(G) + 235.4 \qquad \text{Eq. 10}$$

In some embodiments, the value of the analyte concentration (G) can be corrected in view of the haematocrit level, e.g., using Eq. 11A and 11B.

$$G' = G + \text{Corr for } G < 100 \text{ mg/dL} \qquad \text{Eq. 11A}$$

$$G' = G(1 + \text{Corr}/100) \text{ for } G \geq 100 \text{ mg/dL} \qquad \text{Eq. 11B}$$

In Eq. 11A and 11B, the correction factor Corr can be calculated using sine functions whose amplitude varies with H. For example, at values of H<30% the following equations can be used to calculate Corr.

$$\text{Corr} = -0.4(30-H)\sin(\pi G/400) \text{ for } G < 400 \text{ mg/dL} \qquad \text{Eq. 12A}$$

$$\text{Corr} = 0 \text{ for } G \geq 400 \text{ mg/dL} \qquad \text{Eq. 12B}$$

where the range of Corr is restricted to 0 to −5.

When H>50%, an "asymmetric sine function" can be used where the amplitudes of the positive and negative lobes are different. However, the function is continuous so that there is no sudden step in the correction. For example, Eq. 13A to 13C can be used to calculate Corr for H>50%.

$$Corr = -0.2(H-50)\sin(\pi G/180) \text{ for } G<180 \text{ mg/dL} \quad \text{Eq. 13A}$$

$$Corr = -0.5(H-50)\sin(\pi G/180) \text{ for } 180 \leq G \leq 270 \text{ mg/dL} \quad \text{Eq. 13B}$$

$$Corr = +0.5(H-50) \text{ for } G>270 \text{ mg/dL} \quad \text{Eq. 13C}$$

where the range of Corr is restricted to 0 to −5 for G<180, and 0 to 5 for G≥180.

In another embodiment, the value of the analyte concentration (G) can be corrected in view of the fill time without deriving an estimate of the haematocrit (H), e.g., using Eq. 14A (when G<100 mg/dL) and 14B (when G≥100 mg/dL) in conjunction with Eqs. 15A, 15B, and 15C.

$$G' = G + Corr \text{ for } G<100 \text{ mg/dL} \quad \text{Eq. 14A}$$

$$G' = G(1+Corr/100) \text{ for } G \geq 100 \text{ mg/dL} \quad \text{Eq. 14B}$$

The correction factor Corr in Eq. 14A and 14B can be calculated in view of the fill time (FT) based on a series of threshold values of FT. For example, the following equations can be used to calculate Corr using two threshold values of FT, $Th_1$ and $Th_2$.

$$\text{if } Th_1 < FT < Th_2 \text{ then } Corr = 50(FT - Th_1) \quad \text{Eq. 15A}$$

$$\text{if } FT < Th_1 \text{ then } Corr = 0 \quad \text{Eq. 15B}$$

$$\text{if } FT > Th_2 \text{ then } Corr = 10 \quad \text{Eq. 15C}$$

In an exemplary embodiment, the threshold value $Th_1$ can be about 0.2 seconds and the threshold value $Th_2$ can be about 0.4 seconds. For example, when blood fills the sensor in less than about 0.2 seconds, then its fill behavior can be described as close to ideal. Fill times of less than about 0.2 seconds usually occur when the hematocrit is low enough that that the viscosity of the sample has a minimal effect on the fill behavior of the sample. As a consequence of the low hematocrit, most of the glucose is believe to be partitioned into the plasma phase where it can be oxidized rapidly. Under these conditions, there is little need to correct the glucose result for the effect of fill time, and so the correction factor can be set to zero. Alternatively, when the hematocrit in the sample is high, the viscosity of the sample can affect the fill time of the sample. As a results, the sample can take more than about 0.4 seconds to fill the sensor. As a consequence of the high hematocrit, most of the glucose is believe to be partitioned into the red blood cells and so a lower fraction of the glucose is oxidized. Under these conditions, the glucose result can be corrected in view of the fill time. However, it can be important not to over-correct the glucose value, and so, in an exemplary embodiment, the correction factor can be restricted to a maximum of about 10 mg/dL plasma glucose or about 10% of the signal. An empirically-derived linear equation can be used to gradually increase the correction term in the range of about 0 to about 10 as the fill time increases in the range of about 0.2 to about 0.4 seconds.

One exemplary embodiment of a device that can be used in conjunction with at least some of the systems and methods disclosed herein is a glucose sensor. The glucose sensor can include an electrochemical cell, such as the cell illustrated in FIGS. 2A and 2B. The cell can include a thin strip membrane 201 having upper and lower surfaces 202, 203, and can also include a cell zone 204 defined between a working electrode 206 disposed on the lower surface 203 and a counter/reference electrode 205 disposed on the upper surface 202. The membrane thickness can be selected to achieve a desired result, such as having the reaction products from a counter electrode arrive at a working electrode. For instance, the membrane thickness can be selected so that the electrodes are separated by a distance t, which can be sufficiently close such that the products of electrochemical reaction at the counter electrode can migrate to the working electrode during the time of the test and a steady state diffusion profile can be substantially achieved. Typically t can be less than approximately 500 micrometers, alternatively in the range of about 10 micrometers to about 400 micrometers, and more particularly in the range of about 80 micrometers to about 200 micrometers. In one embodiment a spacing between the electrodes can be selected such that the reaction products from a counter electrode arrive at a working electrode before the end of the assay.

The electrodes can also have a variety of configurations. For instance, the electrodes can be planar. Further, while in the illustrated embodiment the electrodes 205, 206 are facing each other and are substantially opposed, in other embodiments the electrodes can just be facing each other, they can be substantially opposed to each other, or they can have a side-by-side configuration in which the electrodes are positioned approximately in the same plane. Examples of different electrode configurations can be found at least in U.S. Pat. No. 7,431,820 of Hodges, entitled "Electrochemical Cell," and filed on Oct. 14, 2003, the contents of which is hereby incorporated by reference in its entirety.

A sample deposition or "target" area 207 can be defined on the upper surface 202 of the membrane 201 and can be spaced at a distance greater than the membrane thickness from the cell zone 204. The membrane 201 can have a diffusion zone 208 that can extend between the target area 207 and the cell zone 204. A suitable reagent can include a redox mediator M, an enzyme E, and a pH buffer B, each of which can be contained within the cell zone 204 of the membrane and/or between the cell zone 204 and the target area 207. The reagent can also include stabilizers and the like. In use of the sensor, a drop of blood can be placed on the target zone 207, and the blood components can wick towards the cell zone 204.

Figure 2A:
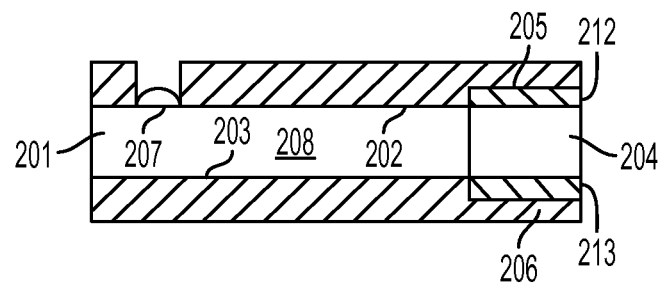
FIG. 2A illustrates a side elevation schematic drawing (not to scale) of an exemplary embodiment of an electrochemical cell in accordance with the present invention.
Figure 2B:
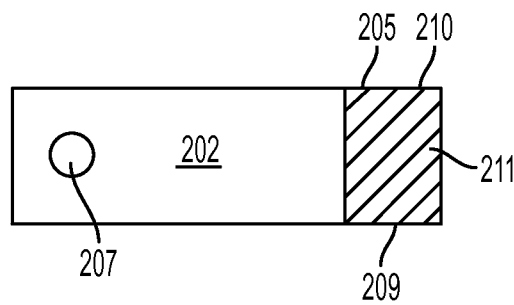
FIG. 2B illustrates a plan view, from above, of the electrochemical cell of FIG. 2A.

Each of electrodes 205, 206 can have a predefined area. In the embodiments of FIGS. 2A and 2B the cell zone 204 can defined by edges 209, 210, 211 of the membrane, which can correspond with edges of the electrodes 205, 206 and by leading (with respect to the target area 207) edges 212, 213 of the electrodes. In the present example the electrodes can be about 600 angstrom thick and can be from about 1 to about 5 mm wide although a variety of other dimensions and parameters can be used without departing from the scope of the present invention.

Alternatively, both sides of the membrane can be covered with the exception of the target area 207 by laminating layers 214 (omitted from plan views) which can serve to prevent evaporation of water from the sample and to provide mechanical robustness to the apparatus. Evaporation of water is believed to be undesirable as it concentrates the sample, allows the electrodes to dry out, and allows the solution to cool, affecting the diffusion coefficient and slowing the enzyme kinetics, although diffusion coefficient can be estimated as above.

Figure 3:
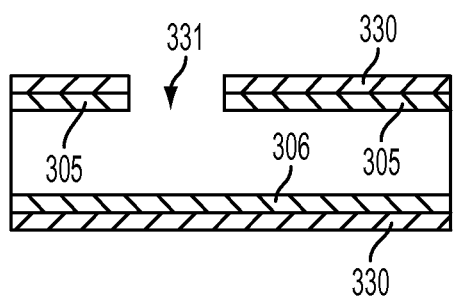
FIG. 3 illustrates a schematic drawing (not to scale), in cross-section, of an exemplary embodiment of a hollow electrochemical cell in accordance with the present invention.

In an alternative embodiment, illustrated in FIG. 3, a hollow electrochemical cell for use with the systems and methods disclosed herein is provided. The electrodes 305, 306 can be supported by spaced apart polymer walls 330 to define a hollow cell. An opening 331 can be provided on one side of the cell whereby a sample can be admitted into the cavity 332.

In this embodiment a membrane is not used, although in some embodiments a membrane can be included. The electrodes can have a variety of configurations, at least as discussed above. By way of non-limiting example, the electrodes can be spaced apart by less than about 500 micrometers, preferably in the range of about 10 or about 20 micrometers to about 400 micrometers, and more preferably in a range of about 80 micrometers to about 200 micrometers. The effective cell volume can be about 1.5 microliters or less.

The electrochemical cells of FIGS. 2A, 2B, and 3 can be used in conjunction with the meters, control units, and other components and steps of the devices, systems, and methods disclosed herein. Further disclosures related to the electrochemical cells of FIGS. 2A, 2B, and 3 are found in U.S. Pat. No. 6,284,125 of Hodges et al., entitled "Electrochemical cell" and filed on Apr. 17, 1998, the contents of which is hereby incorporated by reference in its entirety. For example, electrochemical cells used in conjunction with the present disclosures can have two electrode pairs. The electrode pairs can include any combination of working, counter, counter/reference, and separate reference electrodes.

Another exemplary embodiment of a device that can be used in conjunction with at least some of the systems and methods disclosed herein is the sensor described below and illustrated in FIGS. 4A through 5D. The sensor can be in the form of a form of a test strip 62 including an elongate body 59 that extends along a longitudinal axis L from a proximal end 80 to a distal end 82 and having lateral edges 56, 58. Body 59 can include a proximal sample reaction chamber 61 that contains electrodes 164, 166 and a reagent 72. Test strip body 59 can further include distally positioned electrical contacts 63, 67 for electrically communicating with a test meter (not illustrated).

In one aspect, test strip 62 is formed from multiple layers including a first electrically conductive layer 66, a spacer 60, a second electrically conductive layer 64. First electrically conductive layer 66 and/or second electrically conductive layer 64 can be formed from a variety a conductive materials that are, in one embodiment, positioned on an insulating sheet (not shown). Spacer layer 60 can be formed from a variety of electrically insulating materials and can include, or be formed from, an adhesive. One skilled in the art will appreciate that while a three layer test strip is illustrated, additional electrically conductive or insulative layers could be used to form test strip body 59.

Figure 4A:
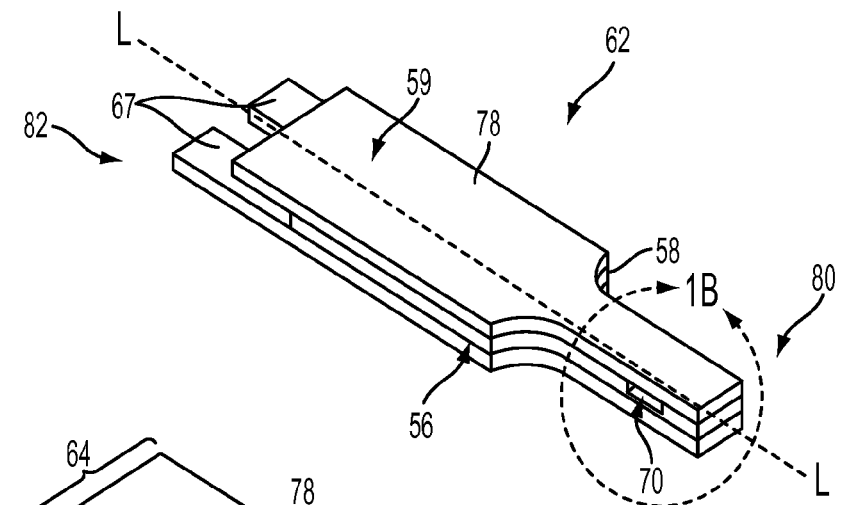
FIG. 4A illustrates a perspective view of an assembled test in accordance with the present invention.
Figure 4B:
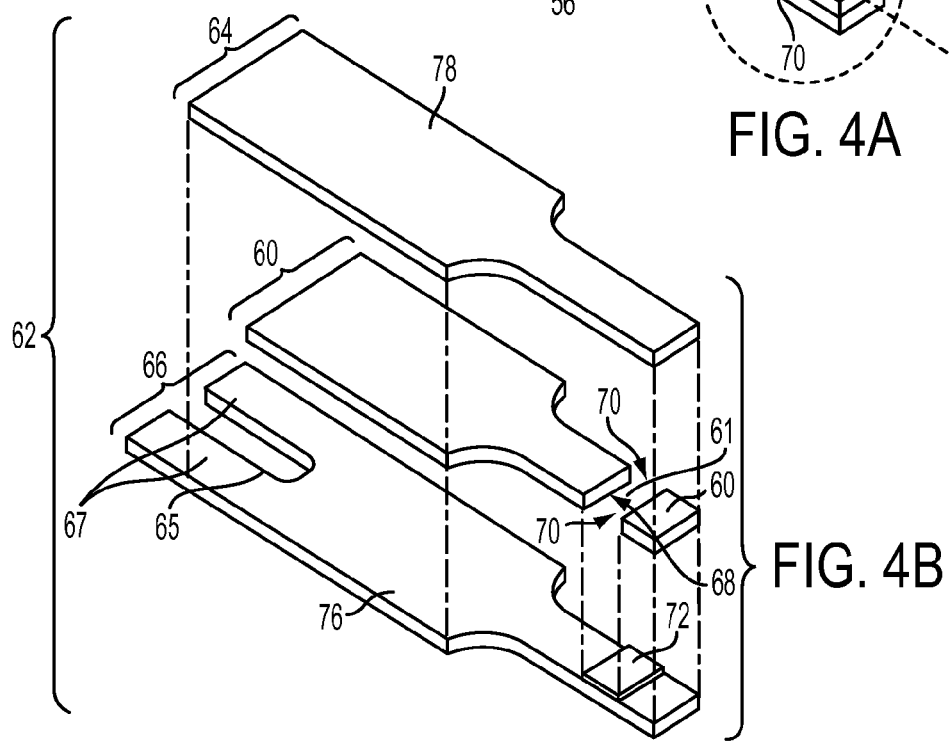
FIG. 4B illustrates an exploded perspective view of an unassembled test strip in accordance with the present invention.
Figure 4C:
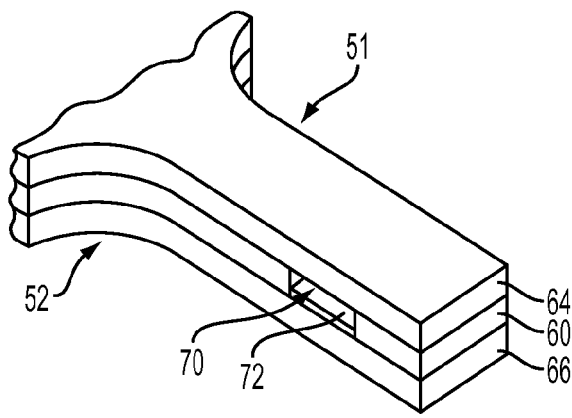
FIG. 4C illustrates an expanded perspective view of a proximal portion of the test strip in accordance with the present invention.

As illustrated in FIGS. 4A through 4C, proximal sample reaction chamber 61 can be defined by first electrically conductive layer 66, second electrically conductive layer 64, and spacer layer 60. As discussed in more detail below, reaction chamber 61 can also include a reagent 72 and first and second electrodes 166, 164. For example, a cutout area 68 in spacer 60 can expose a portion of second electrically conductive layer 64 and first electrically conductive layer 66, and thereby defines first electrode 166 and second electrode 164, respectively. Reagent 72 can be in the form of a layer positioned on first electrode 166.

In one embodiment, reaction chamber 61 is adapted for analyzing small volume samples. For example, sample reaction chamber 61 can have a volume ranging from about 0.1 microliters to about 5 microliters, preferably about 0.2 to about 3 microliters, and more preferably about 0.3 microliters to about 1 microliter. To accommodate a small sample volume, the electrodes are preferably closely spaced. For example, where spacer 60 defines the distance between first electrode 166 and second electrode 164, the height of spacer 60 can be in the range of about 1 micron to about 500 microns, preferably in the range of about 10 microns and about 400 microns, and more preferably in the range of about 40 microns and about 200 microns.

To further assist with the reduction in the volume of reaction chamber 61 the longitudinal and/or lateral dimension of cutout area 68 and/or body 59 can be adjusted. For example, test strip body 59 can include cut-away portions 51, 52 such that the lateral width of reaction chamber 61 is smaller than the full width (widest width) of test strip body 59. Cut-away portions 51, 52 can also facilitate delivery of a sample to reaction chamber 61. For example, cut-away portion 51, 52 can have a shape corresponding to a portion of a finger of a user. When a user expresses a drop of blood with a finger stick, the cut-away portions 51, 52 can help the user align a sample positioned on his/her finger with a sample receiving port (e.g., openings 70) in the lateral edge 56, 58 of body 59. One skilled in the art will appreciate that while two cut-away portions are illustrated, test strip body 59 could include only a single cut-away portion or no cut-away portions.

As stated above, the proximal portion of test strip body 59 can include at least one sample delivery port for delivery of a sample to reaction chamber 61. For example, cutout area 68 can extend transversely to the lateral edges 56, 58 of test strip body 59 to provide two openings 70 for the delivering of physiological fluid to sample reaction chamber 61. Where two openings 70 are present one can act as a sample receiving port for delivery of a fluid sample while the other can act as a vent. One skilled in the art will appreciate that sample can be delivered to sample reaction chamber 61 using alternative structures including sample receiving ports and/or vents positioned at different locations in test strip body 59, such as, for example, sample receiving ports and/or vents positioned in first and/or second electrically conductive layers 66, 64.

In one embodiment, test strip 62 is adapted to draw sample into reaction chamber 61 via capillary action. For example, the dimensions and surface characteristics of reaction chamber 61 and openings 70 can be adapted to produce a capillary force when a liquid sample (e.g., whole blood) is brought into contact with one of openings 70. One skilled in the art will appreciate that reaction chamber 61 can include additional structures to assist with/create capillary forces such as, for example, beads, a porous membrane, and/or other fillers.

As mentioned above, a reagent, such as reagent 72, can be disposed within reaction chamber 61. The composition of reagent 72 can vary depending on the intended analyte and the expected form of the sample. In one aspect, reagent 72 includes at least a mediator and an enzyme and is deposited onto first electrode 166. Various mediators and/or enzymes are within the spirit and scope of the present disclosure. For example suitable mediators include ferricyanide, ferrocene, ferrocene derivatives, osmium bipyridyl complexes, ruthenium (III) hexamine, and quinone derivatives. Examples of suitable enzymes include glucose oxidase, glucose dehydrogenase (GDH) based on pyrroloquinoline quinone (PQQ) co-factor, GDH based on nicotinamide adenine dinucleotide co-factor, and flavine-adenine dinucleotide (FAD) based GDH (FAD-GDH). One exemplary reagent formulation, which would be suitable for making reagent layer 72, is described in U.S. Pat. No. 7,291,256, entitled, Method of Manufacturing a Sterilized and Calibrated Biosensor-Based Medical Device, which is hereby incorporated by reference in its entirety.

Distal to the proximal sample chamber 61, body 59 can include connection tracks that electrically connect first and second electrodes 166, 164 with distal electrical contacts 63, 67. In one aspect, first electrically conductive layer 66 includes a first connection track 76 that electrically connects first electrode 166 with a first electrical contact 67. Similarly, second electrically conductive layer 64 can include a second connection track 78 that connects the second electrode 164 with a second electrical contact 63 (FIG. 5A).

First and second electrically conductive layers can also define first and second electrical contacts 67, 63 that facilitate electrical contact of test strip 62 with a test meter. In one embodiment, a portion of first electrically conductive layer 66 extends distally from the distal end of spacer layer 60 and second electrically conductive layer 64 to define first electrical contact 67. Second electrical contact can be defined by a U-shaped notch 65 in the first electrically conductive layer 66 which exposes a portion of second electrically conductive layer 64. Applicants note that test strip 62 can include a variety of alternative electrical contact configurations for electrically connecting to a test meter. For example, U.S. Pat. No. 6,379,513 discloses electrochemical cell connection structures, and is hereby incorporated by reference in its entirety.

The sensors of FIGS. 4A through 5D can be used in conjunction with the meters, control units, and other components and steps of the devices, systems, and methods disclosed herein. Further disclosures related to the electrochemical cells of FIGS. 4A through 5D are found in U.S. Pat. No. 8,163,162 of Chatelier et al., entitled "Methods And Apparatus For Analyzing A Sample In The Presence Of Interferents," and filed on Mar. 31, 2006 the contents of which is hereby incorporated by reference in its entirety.

Figure 6:
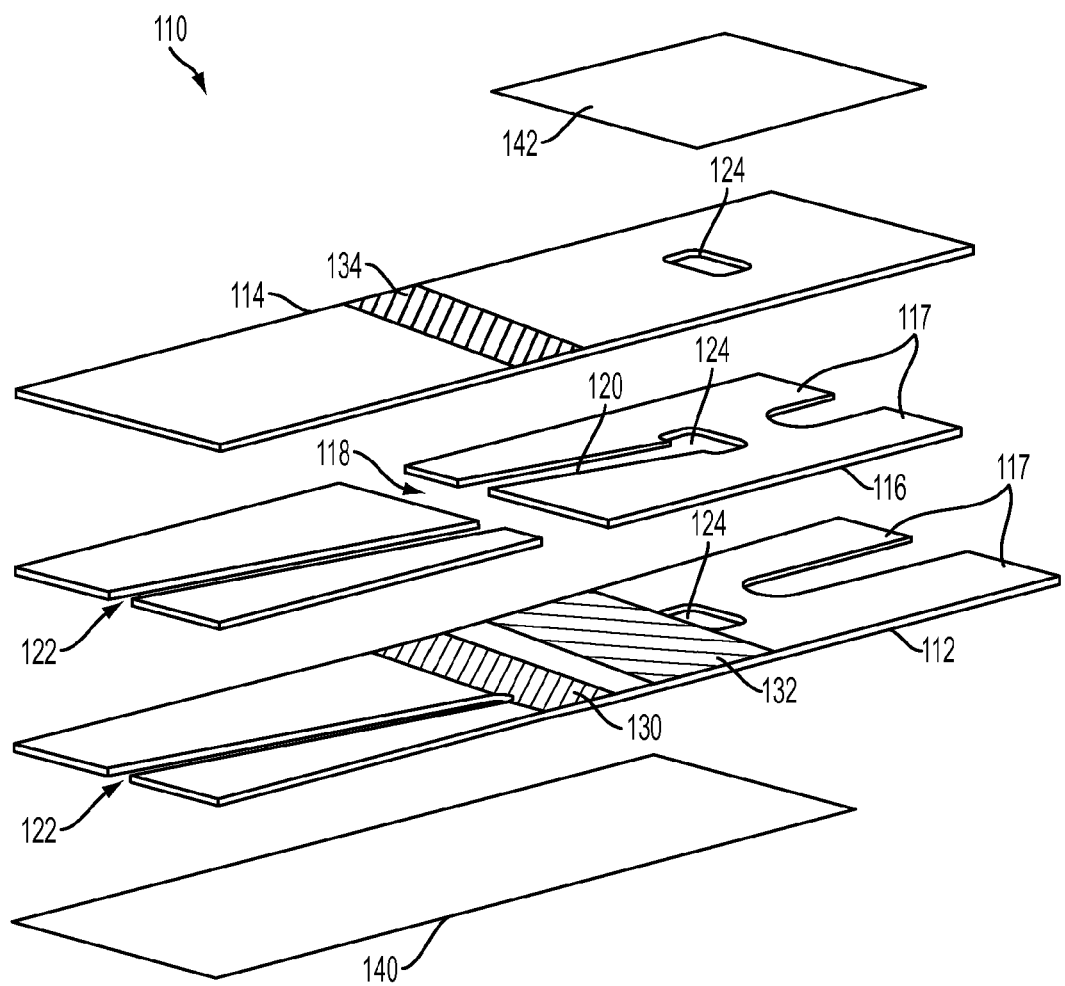
FIG. 6 illustrates an exploded view of an exemplary embodiment of an immunosensor in accordance with the present invention, wherein the immunosensor is configured for use with a control unit having an electrochemical detection system for calculating a fill time.

Another exemplary embodiment of a sample analyzing device for use in conjunction with at least some of the methods disclosed herein, an immunosensor 110, is illustrated in FIG. 6 and is described in U.S. Pat. No. 8,221,994 of Chatelier et al., entitled "Adhesive Compositions for Use in an Immunosensor" and filed on Sep. 30, 2009, the contents of which is hereby incorporated by reference in its entirety. A plurality of chambers can be formed within the immunosensor, including a fill chamber, by which a sample can be introduced into the immunosensor, a reaction chamber, by which a sample can be reacted with one or more desired materials, and a detection chamber, by which a concentration of a particular component of the sample can be determined. These chambers can be formed in at least a portion of a lower electrode, an upper electrode, and a separator of the immunosensor. The immunosensor can also include a vent hole to allow air to enter and escape the immunosensor as desired, and first and second sealing components to selectively seal first and second sides of the vent hole. The first sealing component can also form a wall of the fill chamber.

As illustrated, the immunosensor 110 includes a lower electrode 112 having two liquid reagents 130, 132 striped onto it. The lower electrode 112 can be formed using any number of techniques used to form electrodes, but in one embodiment a polyethylene tetraphthalate (PET) sheet that is filled with barium sulphate is sputter-coated with gold. Other non-limiting example of forming an electrode are disclosed in U.S. Pat. No. 6,521,110 of Hodges et al., entitled "Electrochemical Cell" and filed on Nov. 10, 2000, the contents of which is hereby incorporated by reference in its entirety.

Likewise, the liquid reagents 130, 132 can have a number of different compositions. In one embodiment the first liquid reagent 130 includes an antibody conjugated to an enzyme, such as GDH-PQQ, in a buffer that contains sucrose, as well as a poloxamer, such as Pluronics® block copolymers, an anticoagulant, such as citraconate, and calcium ions. In one embodiment the second liquid reagent 132 includes a mixture of ferricyanide, glucose, and a second mediator, such as phenazine ethosulfate, in an acidic buffer, such as a dilute citraconic acid solution. The first and second liquid reagents 130, 132 can be dried onto the lower electrode 112. A number of techniques can be used to dry the reagents 130, 132, but in one embodiment, following the striping of the reagents 130, 132 on the lower electrode 112, one or more infrared dryers can be applied to the reagents 130, 132. One or more air dryers can also be used, for example, subsequent to the infrared dryers. References to a first reagent and a first liquid reagent and a second reagent and a second liquid reagent herein are used interchangeably and are not necessarily an indication that the reagents are in their liquid or dried form at a given time for a particular embodiment. Further, some of the components associated with the first and second liquid reagents can be used interchangeably and/or in both the first and second liquid reagents as desired. By way of non-limiting example, an anticoagulant can be associated with either or both of the first liquid reagent 130 and the second liquid reagent 132.

A line can be formed in the sputter-coated gold between the reagents 130, 132 such that an edge of reagent 132 is very close to, or touches, the line. The line can be applied using laser ablation or with a sharp metal edge. In one exemplary embodiment the line can be applied before the reagents 130, 132 are striped on the electrode. The line can be designed to electrically insulate the section of the lower electrode 112 under the detection chamber from the section that will be under the reaction chamber. This can provide a better definition of an area of the working electrode during the electrochemical assay.

The immunosensor 110 can also include an upper electrode 114 having one or more magnetic beads 134 containing surface-bound antigens thereon. The antigens can be configured to react with the antibody disposed on the lower electrode 112 and the sample within a reaction chamber 118, as described in further detail below. Applicants note that the components disposed on the lower electrode 112 and on the upper electrode 114 can be interchangeable. Thus, the lower electrode 112 can include one or more magnetic beads 134 and the upper electrode 114 can include two liquid reagents 130, 132 striped onto it. Further, although in the illustrated embodiment the length of the electrode 112 forms the length of the entire body of the immunosensor 110, in other embodiments the electrode can be only a portion of a layer of an immunosensor that serves as the lower or upper electrode or multiple electrodes can be disposed on a single layer of an immunosensor. Further, because voltage applied to the immunosensor can be flipped and/or alternated, each of the lower and upper electrodes can serve as the working electrode and the counter or counter/reference electrode at different stages. For ease of description purposes, in the present application the lower electrode is considered the working electrode and the upper electrode the counter or counter/reference electrode.

A separator 116 disposed between the lower and upper electrodes 112, 114 can have a variety of shapes and sizes, but it generally is configured to desirably engage the lower and upper electrodes 112, 114 to form the immunosensor 110. In one exemplary embodiment, the separator 116 includes adhesive on both sides. The separator 116 can further include a release liner on each side of the two sides of the separator 116. The separator 116 can be cut in a manner that forms at least two cavities. A first cavity can be formed to serve as a reaction chamber 118 and a second cavity can be formed to serve as a detection chamber 120. In one embodiment, the separator 116 can be kiss-cut such that the reaction chamber 118 is aligned with the electrodes 112, 114 to allow an antigen-antibody reaction therein while the detection chamber 120 is aligned with the electrodes 112, 114 to allow for the electrochemical determination of ferrocyanide therein.

In one embodiment, the separator 116 can be placed on the lower electrode 112 in a manner that allows the magnetic beads 134 of the upper electrode 114 and the first reagent 130 of the lower electrode 112 to be at least partially disposed in the reaction chamber 118 and the ferricyanide-glucose combination of the second reagent 132 of the lower electrode 112 to be at least partially disposed in the detection chamber 120. It can be advantageous to include an anticoagulant in each of the first and second liquid reagents 130, 132 so that an anticoagulant is associated with each of the reaction and detection chambers 118, 120. In some embodiments the combination of one of the upper and lower electrodes 112, 114 and the separator 116 can be laminated together to form a bi-laminate, while in other embodiments the combination of each of the lower electrode 112, the upper electrode 114, and the separator 116 can be laminated together to form a tri-laminate. Alternatively, additional layers may also be added.

A fill chamber 122 can be formed by punching a hole into one of the lower and upper electrodes 112, 114 and the separator 116. In the illustrated embodiment the fill chamber is formed by punching a hole in the lower electrode 112 and the separator 116 such that the hole in the lower electrode 112 overlaps the reaction chamber 118. As shown, the fill chamber 122 can be a distance apart from the detection chamber 120. Such a configuration allows a sample to enter the immunosensor 110 through the fill chamber 122 and flow into the reaction chamber 118 to be reacted, for example with the first liquid reagent 130 that includes the antibody conjugated to an enzyme in a buffer on the first electrode 112 and the magnetic beads 134 striped on the upper electrode 114, without entering the detection chamber 120. Once the sample has been reacted, it can then flow into the detection chamber 120 for interaction with the second liquid reagent 132, for example the mixture of ferricyanide, glucose, and the second mediator in an acidic buffer.

A vent 124 can be formed by punching a hole through each of the two electrodes 112, 114 and the separator 116 such that the vent 124 extends through the entirety of the immunosensor 110. The hole can be formed in a suitable manner, such as, for example, drilled or punched in a number of different locations, but in one exemplary embodiment it can overlap a region of the detection chamber 120 that is spaced apart from the reaction chamber 118.

The vent 124 can be sealed in a number of different manners. In the illustrated embodiment, a first sealing component 140 is located on the lower electrode 112 to seal a first side of the vent 124 and a second sealing component 142 is located on the upper electrode 114 to seal a second side of the vent 124. The sealing components can be made of and/or include any number of materials. By way of non-limiting example, either or both of the sealing components can be hydrophilic adhesive tape or Scotch® tape. Adhesive sides of the sealing components can face the immunosensor 110. As shown, not only can the first sealing component 140 form a seal for the vent 124, but it can also form a wall for the fill chamber 122 so that the sample can be contained therein. Properties incorporated onto the adhesive side of the first sealing component 140 can be associated with the fill chamber 122. For example, if the first sealing component 140 includes properties making it hydrophilic and/or water soluble, the fill chamber can remain well-wet when a sample is disposed therein. Further, the sealing components 140, 142 can be selectively associated and disassociated with the immunosensor 110 to provide venting and/or sealing for the immunosensor 110 and the components disposed therein as desired.

Adhesives can generally be used in the construction of the immunosensor. Non-limiting examples of ways in which adhesives can be incorporated into immunosensors and other sample analyzing devices of the present disclosure can be found in U.S. Pat. No. 8,221,994 of Chatelier et al., entitled "Adhesive Compositions for Use in an Immunosensor" and filed on Sep. 30, 2009, the contents of which was already incorporated by reference in its entirety.

While the present disclosure discusses a variety of different embodiments related to immunosensors, other embodiments of immunosensors can also be used with the methods of the present disclosure. Non-limiting examples of such embodiments include those described in U.S. Patent Application Publication No. 2003/0180814 of Hodges et al., entitled "Direct Immunosensor Assay" and filed on Mar. 21, 2002, U.S. Patent Application Publication No. 2004/0203137 of Hodges et al., entitled "Immunosensor" and filed on Apr. 22, 2004, U.S. Patent Application Publication No. 2006/0134713 of Rylatt et al., entitled "Biosensor Apparatus and Methods of Use" and filed on Nov. 21, 2005, and U.S. patent application Ser. No. 12/563,091, published as U.S. Patent Application Publication No. 2010/0006452 A1, which claims priority to each of U.S. Patent Application Publication Nos. 2003/0180814 and 2004/0203137, each of which is hereby incorporated by reference in its entirety.

In one embodiment, the immunosensor 110 can be configured to be placed into a meter that is configured to apply a potential to the electrodes 112, 114 and measure a current that results from the application of the potential. In one embodiment, the immunosensor includes one or more tabs 117 for engaging a meter. Other features can also be used to engage the immunosensor 110 with a meter. The meter can include a number of different features. For example, the meter can include a magnet that is configured to maintain certain components of the immunosensor 110 in one chamber while other components flow to the other. In one exemplary embodiment, the magnet of the meter is located such that, upon placing the immunosensor 110 in the meter, the magnet is disposed below the reaction chamber 118. This can allow the magnet to assist in holding back any magnetic beads 134, and more particularly any antibody-enzyme conjugate that is bound to the beads 134, from flowing into the detection chamber 120.

An alternate feature of the meter includes a heating element. A heating element can help speed up the reaction rate and help the sample flow through the immunosensor 110 in a desired manner by reducing the viscosity. A heating element can also allow one or more chambers and/or a sample disposed therein to be heated to a predetermined temperature. Heating to a predetermined temperature can help provide accuracy, for example, by diminishing or removing the effects of temperature change as reactions occur.

Further, a piercing instrument can also be associated with the meter. The piercing instrument can be configured to pierce at least one of the first and second sealing components at a desired time so that air can flow out of the vent hole and liquid can flow from the reaction chamber into the detection chamber.

The immunosensor 110 can also be configured to be associated with a control unit. The control unit can be configured to perform a variety of functions. In one exemplary embodiment, the control unit is capable of measuring a fill time of a sample when it is introduced to the device. In another embodiment, the control unit can be configured to determine a haematocrit value of a blood sample. In yet another embodiment, the control unit is configured to calculate a concentration of an analyte in the sample in view of the fill time. In fact, the control unit can include a number of different features, depending, at least in part, on the functionality desired and the method by which the system is designed to measure the fill time.

The control unit can also measure other aspects of the system. By way of non-limiting example, the control unit can be configured to measure a temperature of one or more chambers of the immunosensor. It can also be configured to measure a temperature of the sample, a color of the sample, or a variety of other characteristics and/or properties of the sample and/or the system. By way of further non-limiting example, the control unit can be configured to communicate the results of the fill time determination, the results of the analyte concentration determination, and/or the haematocrit measurement to outside equipment. This can be accomplished in any number of ways. In one embodiment, the control unit can be hardwired to a microprocessor and/or a display device. In another embodiment, the control unit can be configured to wirelessly transmit data from the control unit to a microprocessor and/or a display device.

Other components of the system can also be configured to make such measurements. For example, the immunosensor or the meter can be configured to measure a temperature of one or more chambers of the immunosensor, measure or infer the temperature of a sample, or measure, determine, or infer a variety of other characteristics and/or properties of the sample and/or the system. Still further, Applicants note that these features of a control unit can be interchanged and selectively combined in a single control unit. For example, a control unit can both determine a fill time and measure a temperature of a chamber. In other embodiments, multiple control units can be used together to perform various functions, based at least in part on the configurations of the various control units and the desired functions to be performed.

EXAMPLE 1

The use of an electrochemical system to measure fill time is demonstrated by the following example. In the following example, the system included a sensor with two opposed electrodes, with reagents designed to react with the sample dried on one electrode. A plurality of samples was provided for analysis to test the performance of the systems, devices, and methods disclosed herein. The samples were blood samples that contained three different levels of haematocrit, which were known so comparisons of the test results could be compared to the actual results to determine the accuracy of the systems, devices, and methods. The four levels of haematocrit were approximately 20%, 60%, and 75%. Testing three levels of haematocrit allowed the accuracy of the disclosed systems, devices, and methods to be confirmed over a broad spectrum of concentration levels.

Figure 7:
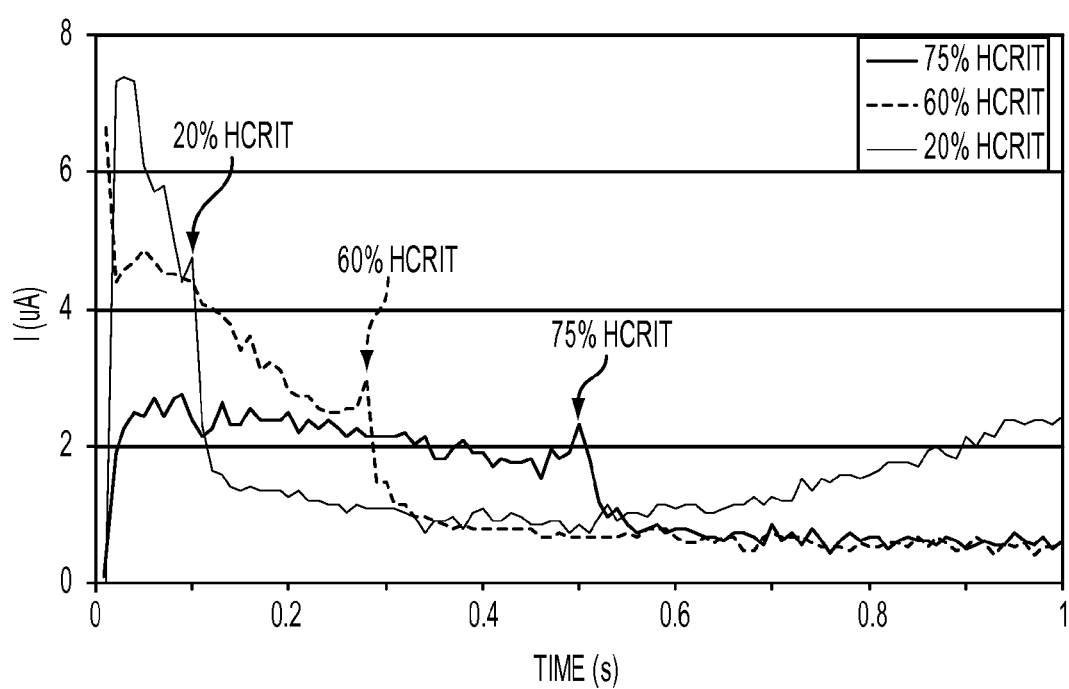
FIG. 7 illustrates a plot of a current versus time transient performed using an exemplary embodiment of an electrochemical cell in conjunction with an exemplary embodiment for testing a variety of blood samples provided herein.

In this example the electrode covered with the dried reagent is the second electrode. The first and second electrodes cover the entire area of the chamber to be filled with liquid sample. Samples were introduced into the sensor. While the introduction of samples into the sensor could have been accomplished in a variety of manners, in this example each sample was admitted individually by way of capillary action into the fill chamber. As soon as the blood started to enter the detection chamber, a 300 mV potential was applied to the electrodes by way of the meter for approximately four seconds. Alternatively, the voltage could have been applied prior to or while the blood was arriving in the detection chamber. A plot of the current versus time transient resulting from this example is illustrated in FIG. 7. As shown in the FIG. 7, the line showing the time-current transient obtained with 75% haematocrit blood is relatively flat from about 0.1 to about 0.5 seconds since the filling process increases the area of the first electrode (which would tend to increase the current) and at the same time there is electrochemical depletion of electroactive species at the first electrode (which would tend to decrease the current). These two processes are approximately matched while the sensor is filling with blood. After fill is complete (at approximately 0.5 s) the first process is over and the second process dominates so that the current drops abruptly. The latest time at which the current decreases sharply is taken as the fill time. The results for 20% and 60% haematocrit blood showed similar results, with a current drop at approximately 0.3 s for 60% haematocrit blood and at approximately 0.1 s for 20% haematocrit blood. The results of this experiment demonstrated the feasibility of using a measurement of current to determine the haematocrit percentage of blood.

EXAMPLE 2

Figure 8:
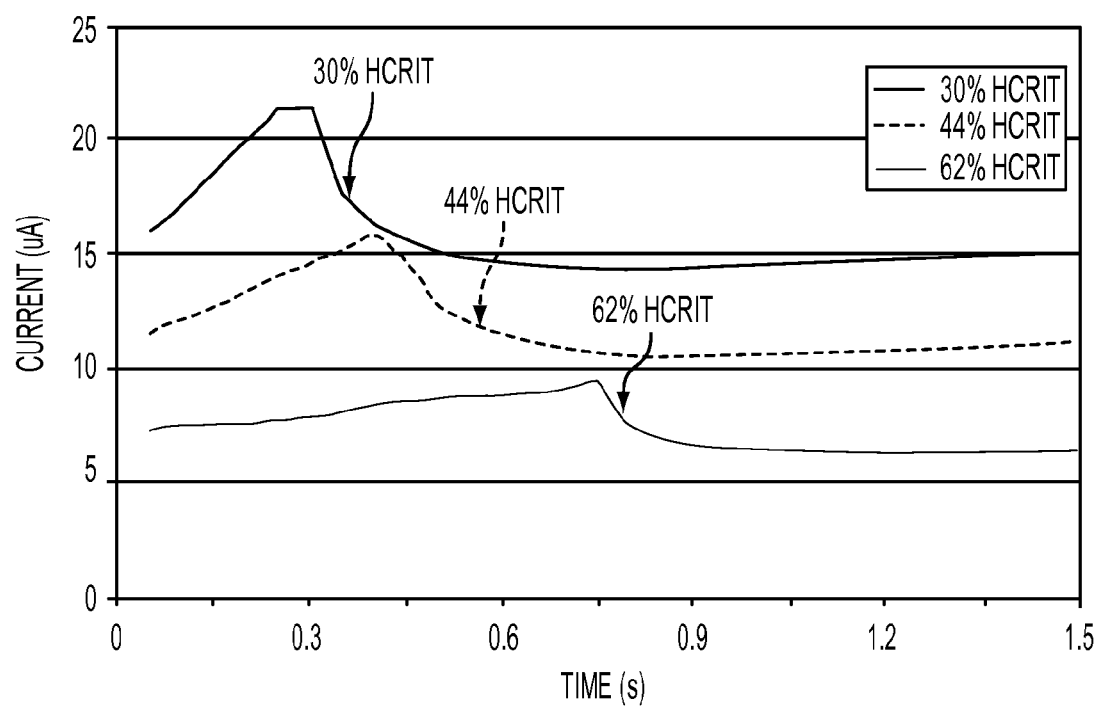
FIG. 8 illustrates a plot of a current versus time transient performed using another exemplary embodiment of an electrochemical cell in conjunction with an exemplary embodiment for testing a variety of blood samples provided herein.

A second type of sensor was constructed which included two opposed electrodes with reagents designed to react with the sample dried on one electrode. In this example however the electrode with the dried reagent was the first electrode and was configured such that it did not cover the entire area of the liquid filled chamber whereas the second electrode was configured such that it covered a wider area of the liquid filled chamber and was contacted with liquid prior to the first electrode being contacted with liquid. When this sensor was used to test a plurality of blood samples adjusted to various haematocrits, the pattern of currents obtained shown in FIG. 8 was obtained. In this Example, the four levels of haematocrit were approximately 30%, 44%, and 62%. As shown in FIG. 8, the early part of each trace corresponds to the period during which the filling process increases the area of the working electrode and hence increases the current. When the fill process is complete, the electrochemical depletion of electroactive species tends to decrease the current at the time indicated by the arrows in the figure. Once again, the time at which the current decreases sharply is taken as the fill time. The different configuration of the sensors leads to a different dependence of fill time on haematocrit.

EXAMPLE 3

The use of variable prepulse times in an electrochemical system is demonstrated by the following example. A potentiostat meter was constructed which was capable of using the fill time information to vary the prepulse time using the methods discussed above. An initial test of the new meters was performed using heparinised capillary blood. The natural haematocrit and glucose were tested, and then plasma and 77% blood were tested at the natural or spiked glucose levels. Strips were tested on the original (fixed time) meters and on the meters which incorporated the variable prepulse time algorithm disclosed above. The data were analyzed using the algorithm discussed above.

Figure 9:
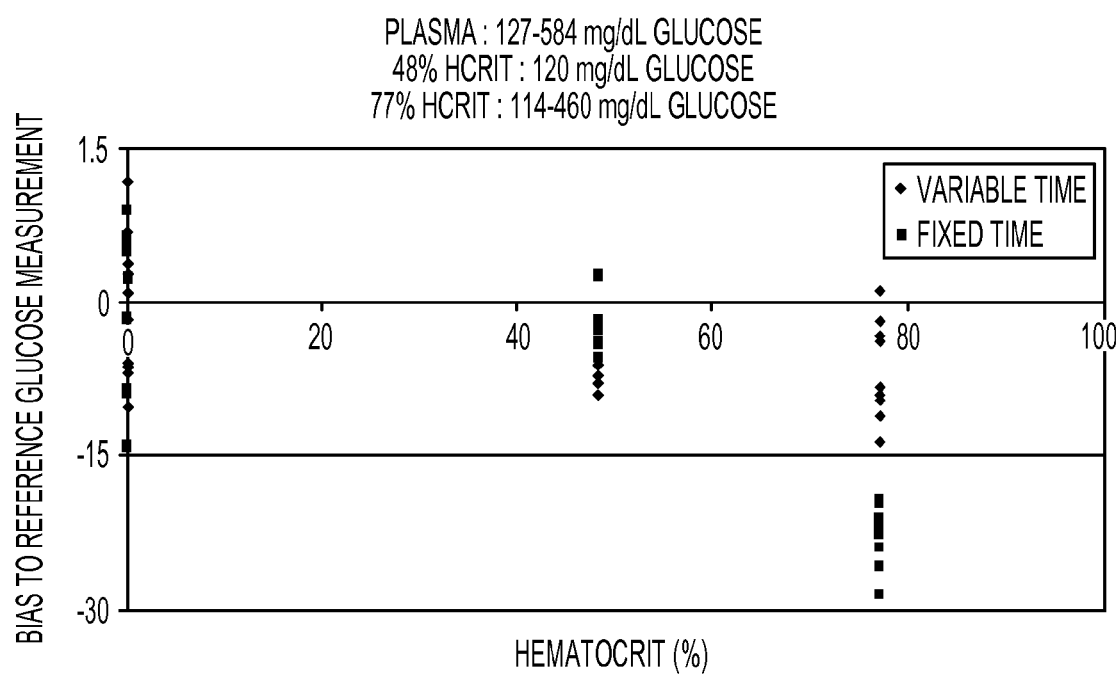
FIG. 9 illustrates a plot of the results of testing a variety of blood samples using a variable prepulse time method according to an exemplary embodiment and a fixed time method.

FIG. 9 shows that the 77% haematocrit blood gave negative biases (−19 to −28%) when tested with the original (fixed time) meters, but that all points were within 15% of the reference glucose measurement when tested with the variable prepulse time meters. An example of a commercially available instrument configured to perform a reference glucose measurement is a Yellow Springs Instrument (YSI) glucose analyzer. The overall statistics for the two types of meters are summarized in Table 1, below.

TABLE 1

| Parameter | Fixed time meters | Variable time meters |
|---|---|---|
| Mean CV (%) | 3.6 | 3.0 |
| Mean bias | −9.4 | −4.4 |
| Global SD bias | 12.0 | 5.9 |
| % biases within 15% | 62 | 100 |

As shown in Table 1, the variable time meters outperformed the fixed time meters in terms of accuracy and precision.

EXAMPLE 4

The use of an electrochemical system to determine haematocrit on the basis of fill time is demonstrated by the following example. In this example, the system included a sample analyzing device, in particular the immunosensor 110 of FIG. 6, a meter configured to apply a potential, and a control unit configured to determine the initial fill velocity. In particular, a potential was applied to the electrodes of the immunosensor 110, a level of haematocrit was determined, and then the potential was reversed. The concentration of the analyte was subsequently determined in view of the determined level of haematocrit. The level of haematocrit was determined in view of a fill time of the sample.

A plurality of samples was provided for analysis to test the performance of the systems, devices, and methods disclosed herein. The samples were blood samples that contained C-reactive proteins, and thus the concentration of the analyte being determined was the concentration of C-reactive proteins. The samples contained four different levels of haematocrit, which were known so comparisons of the test results could be compared to the actual results to determine the accuracy of the systems, devices, and methods. The four levels of haematocrit were approximately 15%, 49%, 60%, and 72%. Testing four levels of haematocrit allowed the accuracy of the disclosed systems, devices, and methods to be confirmed over a broad spectrum of concentration levels.

In this example, an immunosensor was preheated to approximately 37° C. before a sample was introduced. The meter associated with the immunosensor was configured to perform the preheating, although other alternatives could have been used. Samples were then introduced into the immunosensor. While the introduction of samples into the immunosensor could have been accomplished in a variety of manners, in the example each sample was admitted individually by way of capillary action into the fill chamber.

Figure 10:
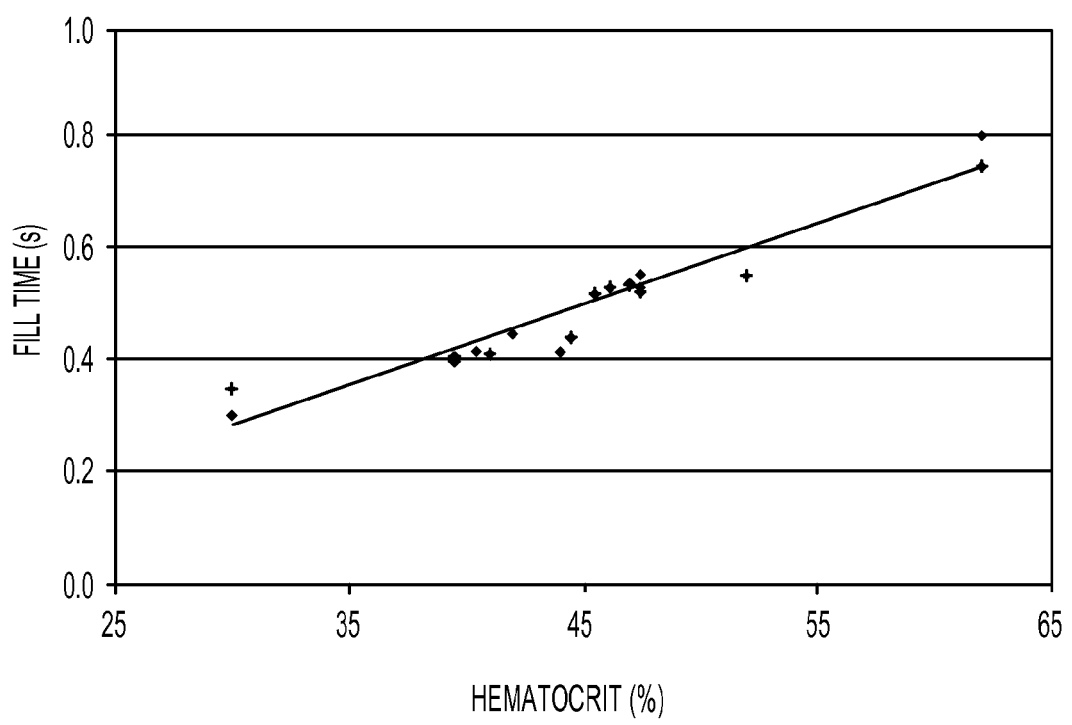
FIG. 10 illustrates a plot of fill time versus haematocrit level for a variety of blood samples provided herein.

After approximately two minutes had elapsed, the vent of the immunosensor was accessed by piercing the first sealing component. A piercing instrument of the meter was used to perform the piercing action, which in turn allowed the blood to flow from the reaction chamber of the immunosensor into the detection chamber of the immunosensor. As the blood entered the detection chamber, a 300 mV potential was applied to the electrodes by way of the meter. As in the examples discussed above, the current versus time transient was used to determine the fill time of the sample according to the methods discussed above. A plot of the fill time versus haematocrit percentage from this example is illustrated in FIG. 10. In some embodiments, the estimate of the haematocrit according to the methods disclosed herein can be used to express the antigen concentration with respect to plasma rather than whole blood, since this is more acceptable in pathology.

As discussed above, in some embodiments it may be desirable to only measure a level of haematocrit. Thus, the first calculation based on the initial current may be the only step that is needed to make that calculation. The actual determination of the haematocrit level can be determined as quickly as the initial current can be calculated. Thus, by way of non-limiting example, if the initial current is calculated based on an average over the first 50 milliseconds, the level of haematocrit can be determined following the first 50 milliseconds. Thus, measurements of a haematocrit level of a blood sample can be performed in less than one second.

EXAMPLE 5

Figure 11:
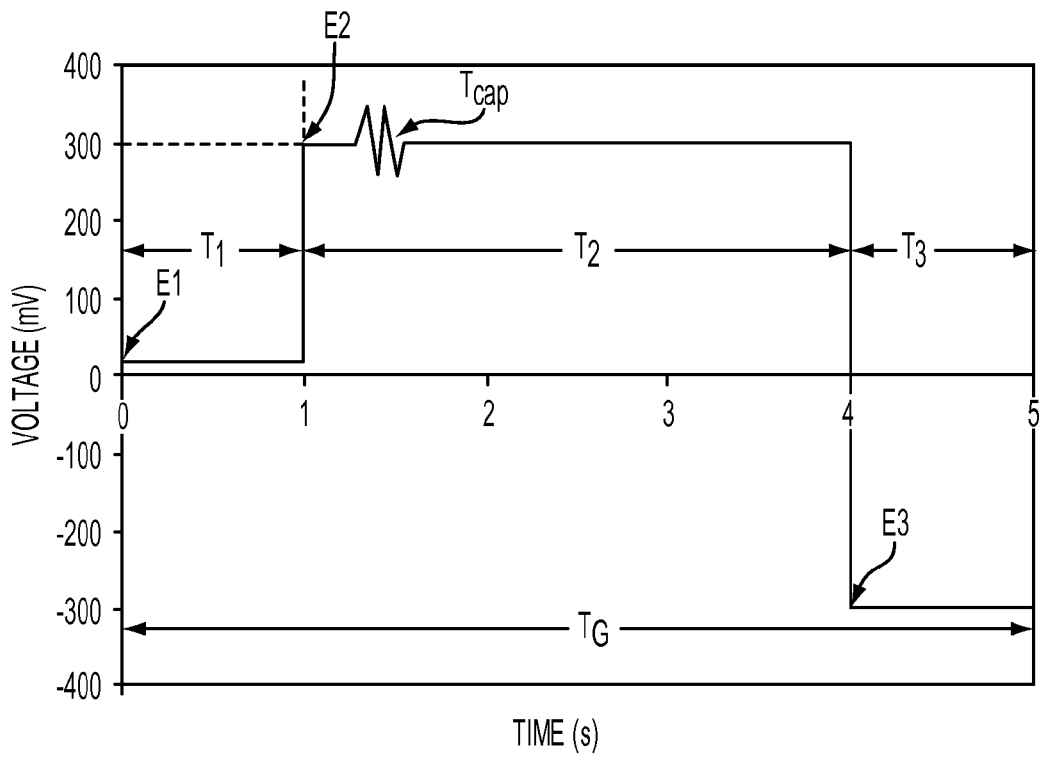
FIG. 11 illustrates a test voltage waveform in which the test meter applies a plurality of test voltages for prescribed time intervals.

An exemplary algorithm for correcting an analyte measurement based on fill time of a sample without further derivation of and correction for hematocrit is demonstrated by the following example. In this example, a sensor which contained the enzyme FAD-GDH, instead of GDH-PQQ, was tested. A blood sample containing glucose was applied to the sensor and the potential waveform shown in FIG. 11 was applied. A fill time of the sample was determined during the application of the first potential to the sensor (E1, which was about +20 mV in this example) for about 1 second. In this example, the fill time was determined to be the period of time from the first detection of sample in the sensor until the time at which the maximum value of the rate of change of the current transient during application of the first potential was measured, i.e., the maximum value of $i(t)-i(t+dt)$. The maximum value of $i(t)-i(t+dt)$, i.e., the sharpest drop in current, corresponds to the time at which a sufficient volume of the sample has filled the sensor for the analyte measurement to be conducted. The fill time was not assessed during the approximately first 0.15 seconds following sample detection, since the initial signal is a combination of the rapid current decrease due to the consumption of antioxidant species near the anode and the slower current increase which accompanies filling of the sensor. When these two rates are matched then a pseudo steady state current is achieved and there is little change in current while the rest of the sensor fills with blood. For this reason, the earliest fill time shown in FIG. 11 is about 0.15 seconds.

Following application of the first potential (E1, for about 1 second), a second test potential E2 of +300 mV was applied for about 3 seconds after which a third test potential E3 of −300 mV was applied. Values of $i_l$ and $i_r$ were calculated using Eqs. 2b and 3b. A value of $i_l$ was calculated as the sum of currents from 3.9 to 4 seconds of the 5 second long period and a value of $i_r$ was calculated as the sum of currents from 4.25 to 5 seconds of the 5 second long period. A first glucose concentration in the sample was then calculated using Eq. 1, above. In this example, the values of p, a and zgr were 0.5796, 0.02722 and 1.8, respectively.

The first glucose concentration was then corrected in view of the fill time of the sample according to Eqs. 14A, 14B, 15A, 15B, and 15C, above, for which the two threshold values of FT, $Th_1$ and $Th_2$ were 0.2 seconds and 0.4 seconds, respectively. As will be discussed in the following examples, Applicants found that the results of glucose measurements corrected in view of fill time according to Eqs. 14A, 14B, 15A, 15B, and 15C improved accuracy resulting in a lower bias from reference data.

EXAMPLE 6

Figure 12:
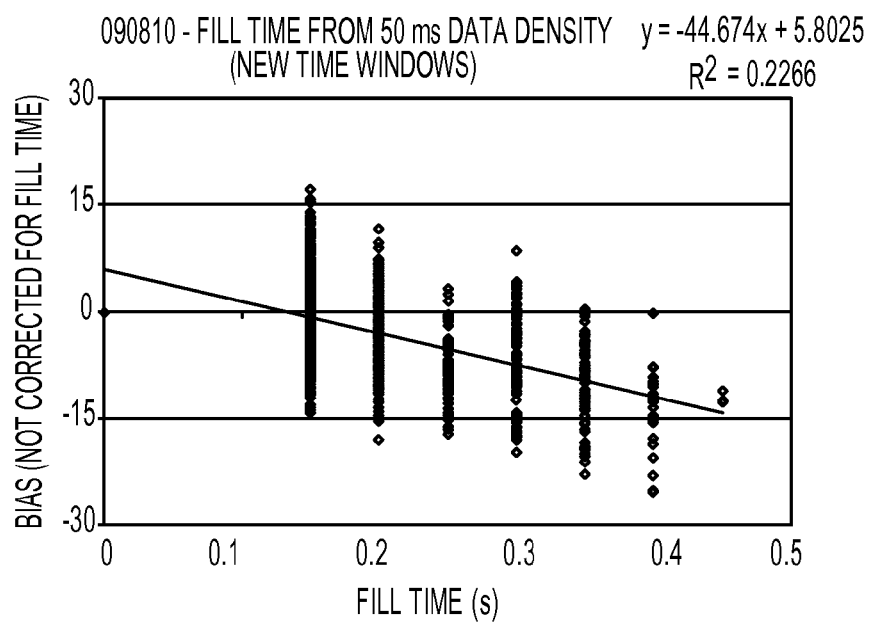
FIG. 12 illustrates a plot of the results of testing a variety of blood samples without correcting for fill time.

The dependence of bias from reference values of concentration on the fill time of samples is demonstrated in this example. Samples with a range of hematocrit from about 0 to about 70% were tested using FAD-GDH sensors according to the algorithms discussed above, but were not corrected for fill time. FIG. 12 shows that the bias of samples from reference values of analyte concentration was dependent on the fill time of the sample. For example, as shown in FIG. 12, the bias of samples was increasingly negative as fill time increases. In other words, the accuracy of uncorrected values of analyte concentration decreased for samples with longer fill times. Thus, there is a distinct dependence of the bias on the fill time of samples.

EXAMPLE 7

Figure 13A:
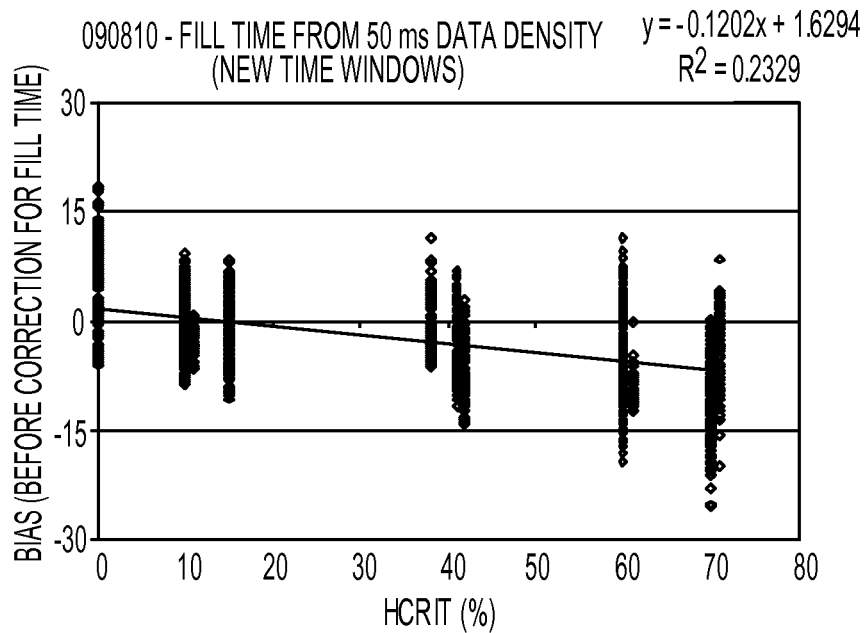
FIG. 13A illustrates the same data as FIG. 12 plotted against the hematocrit of the samples.
Figure 13B:
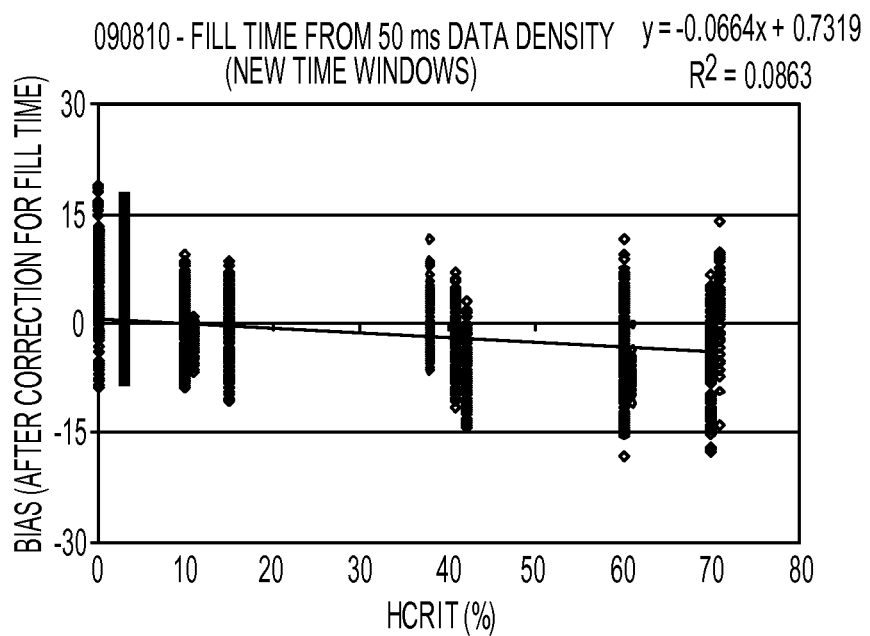
FIG. 13B illustrates a plot of the data shown in FIG. 12 corrected for fill time and plotted against the hematocrit of the sample.

The improvement resulting from correcting analyte concentration in view of fill time is demonstrated in this example. FIG. 13A shows the same data set as shown in FIG. 12 plotted against the hematocrit range of the samples. FIG. 13B shows the improvement obtained when the data is corrected in view of fill time according to Eqs. 14A, 14B, 15A, 15B, and 15C, above. As illustrated in FIGS. 13A and 13B, the global SD bias decreased from 6.2 to 5.7 after the data was corrected for fill time. Thus, correcting for fill time according to the above algorithms provides improved accuracy.

EXAMPLE 8

Figure 14:
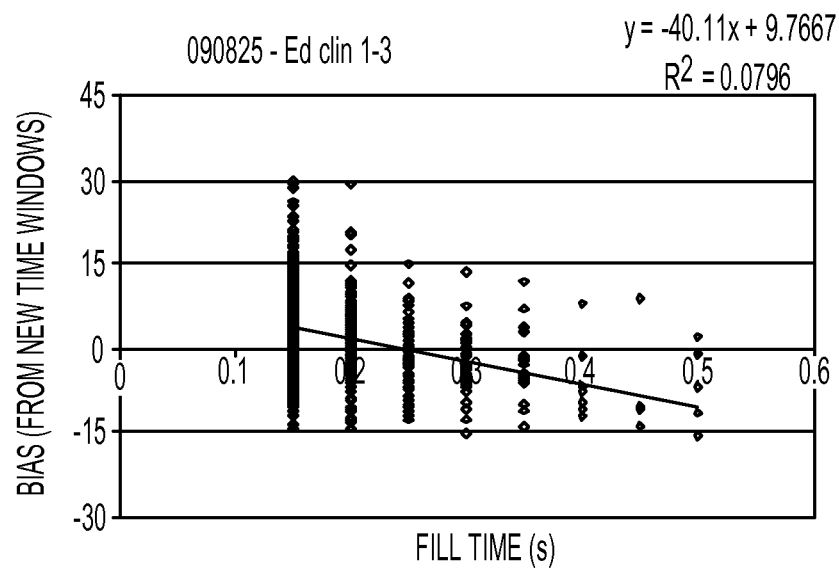
FIG. 14 illustrates a plot of the results of testing a variety of blood samples in a clinical setting.

Increased accuracy using fill time correction in a clinical setting is demonstrated by this example. FIG. 14 illustrates a plot of the bias versus fill time data for samples obtained from 311 donors tested using FAD-GDH sensors in a clinical setting according to the algorithms discussed above in Example 5. For this data set, the fill time correction provided a decrease in global SD bias from 5.75 to 5.58. The improvement in this clinical data was only modest because most samples filled the sensor in about 0.2 seconds or less, and were this uncorrected by the fill time algorithm.

EXAMPLE 9

Figure 15:
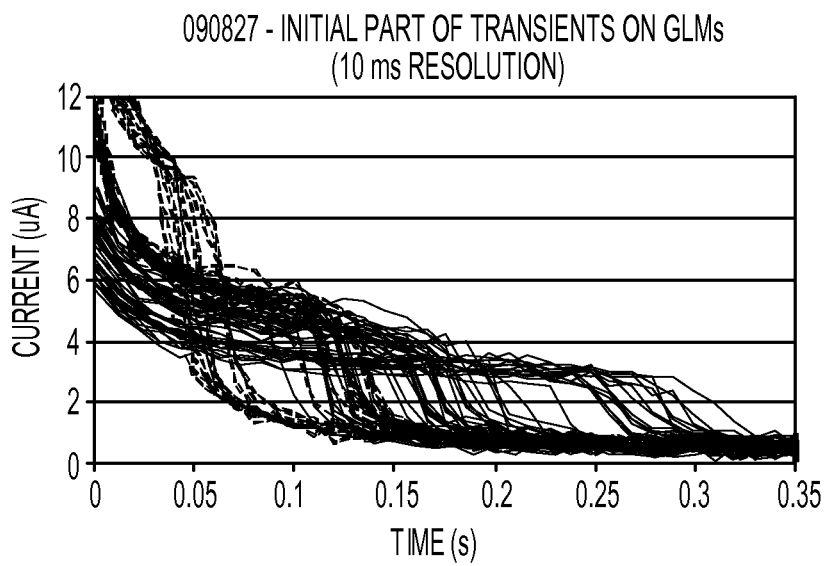
FIG. 15 illustrates a plot of current versus time transients obtained when blood with hematocrits in the range of 15% to 72% was loaded into another exemplary embodiment of an electrochemical sensor in conjunction with an exemplary embodiment for testing a variety of samples provided herein.
Figure 16:
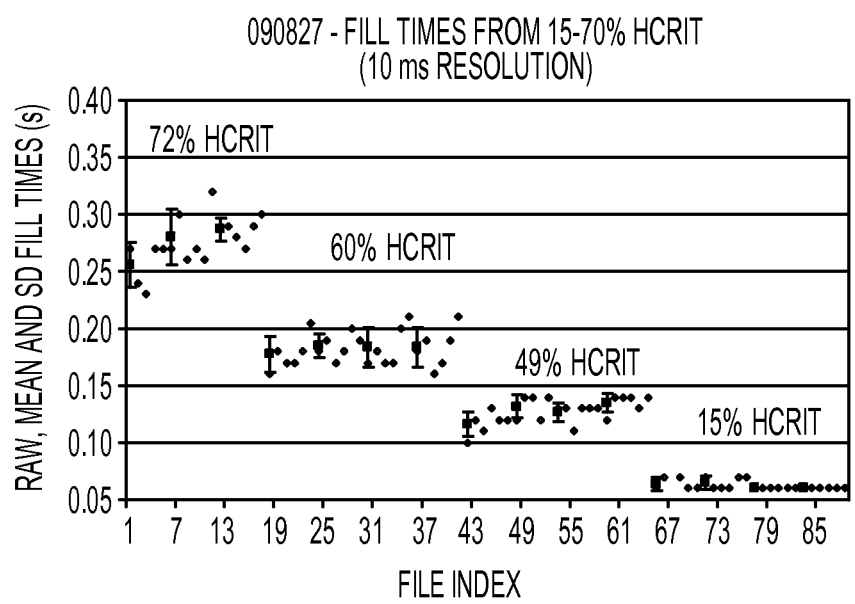
FIG. 16 illustrates an alternate plot of the data shown in FIG. 15.

The data in the previous examples were obtained at 50 ms data density (i.e., one current value was stored every 50 ms). Better resolution in fill times can be obtained with faster data storage, e.g., 10 ms data density, as shown in FIG. 15. FIG. 15 illustrates the current transients obtained when blood with hematocrits in the range of about 15% to about 72% was loaded into sensors. FIG. 16 illustrates fill time data calculated from the data of FIG. 15. FIG. 16 shows the raw fill time values as open diamonds, the mean of 5 replicates as filled squares, and ±1 SD as vertical bars. As shown in FIG. 16, the fill times ranged from about 0.06 seconds to about 0.32 seconds, with higher hematocrit samples filling more slowly. When the data presented in this example was tested for glucose concentration, the global SD bias decreased from 5.08 to 4.71 after the glucose values were corrected for fill time using the algorithms discussed above in Example 5.

Applicants note that these nine examples are merely nine of many examples of how the teachings contained herein can be performed and used. Further, although the methods, systems, and devices disclosed herein are primarily used in conjunction with determining a concentration of an analyte of a blood sample, and are primarily focused on accounting for errors that can result from varying fill times and levels of haematocrit in blood samples, Applicants note that the disclosures contained herein can also be used for a variety of other samples containing analytes and can test for a variety of antigens and/or antibodies contained within a sample.

Applicants note that to the extent various methods, systems, and devices rely on a particular equation, the equations provided are generally based on the examples to which the equations were applied. One skilled in the art, in view of the present disclosure, will be able to make adjustments to the disclosed equations for other situations without departing from the scope of the invention.

Still further, the methods discussed herein, such as those related to determining a concentration and using the systems and devices, are also not limited by the particular steps or order of the steps, except where indicated. One skilled in the art will recognize various orders in which the methods can be performed, and further, will recognize that steps can be modified or added without departing from the scope of the invention.

Non-limiting examples of some of the other types of devices with which the methods disclosed herein can be used are discussed in greater detail in U.S. Pat. No. 5,942,102 of Hodges et al., entitled "Electrochemical Method" and filed on May 7, 1997, U.S. Pat. No. 6,174,420 of Hodges et al., entitled "Electrochemical Cell" and filed on May 18, 1999, U.S. Pat. No. 6,379,513 of Chambers et al., entitled "Sensor Connection Means" and filed on Sep. 20, 1999, U.S. Pat. No. 6,475,360 of Hodges et al., entitled "Heated Electrochemical Cell" and filed on Sep. 11, 2000, U.S. Pat. No. 6,632,349 of Hodges et al, entitled "Hemoglobin Sensor" and filed on Jul. 14, 2000, U.S. Pat. No. 6,638,415 of Hodges et al., entitled "Antioxidant Sensor" and filed on Jul. 14, 2000, U.S. Pat. No. 6,946,067 of Hodges et al., entitled "Method of Forming an Electrical Connection Between an Electrochemical Cell and a Meter" and filed on Dec. 9, 2002, U.S. Pat. No. 7,043,821 of Hodges, entitled "Method of Preventing Short Sampling of a Capillary or Wicking Fill Device" and filed on Apr. 3, 2003, and U.S. Pat. No. 7,431,820 of Hodges et al., entitled "Electrochemical Cell" and filed on Oct. 1, 2002, each of which is hereby incorporated by reference in its entirety.

Further, to the extent the disclosures herein are discussed for use with a device having a particular configuration, any number of configurations can be used. For example, some configurations that can be used with the present disclosures include sensors having two electrodes facing each other, sensors having two electrodes on the same plane, and sensors having three electrodes, two of which are opposed and two of which are on the same plane. These different configurations can occur in any number of devices, including immunosensors and the other aforementioned devices.

Various aspects of the devices, systems, and methods can be adapted and changed as desired for various determinations without departing from the scope of the present invention. Further, one skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method for determining a concentration of an analyte in a sample, the method comprising:
    detecting a presence of the sample in an electrochemical sensor having two spaced electrodes;
    determining a fill time of the sample in the electrochemical sensor;
    calculating a prepulse time using the determined fill time;
    reacting an analyte to cause a physical transformation of the analyte between the two electrodes;
    applying a potential between the two spaced electrodes for a time period equal to the prepulse time;
    determining a first concentration of the analyte in the sample using the two electrodes;

calculating a correction factor in view of the determined fill time; and determining a corrected analyte concentration based on the first analyte concentration and the correction factor.

2. The method of claim 1, wherein determining the fill time includes:
applying an electric potential between the two electrodes while the sample is introduced; and
measuring a current as a function of time; and
determining a current drop time based on the current as a function of time,
wherein the current drop time corresponds to the fill time of the sample.

3. The method of claim 2, wherein determining the current drop time comprises calculating the maximum negative value of the change in the measured current over time.

4. The method of claim 2, wherein determining the current drop time comprises calculating a difference between at least two current values where the difference is greater than a first predetermined threshold.

5. The method of claim 2, wherein determining the current drop time comprises calculating a difference between at least two current values where the difference is less than a second predetermined threshold.

6. The method of claim 2, wherein determining the current drop time comprises calculating a slope in the measured current as a function of time where the slope is greater than a third predetermined threshold.

7. The method of claim 2, wherein determining the current drop time comprises calculating a slope in the measured current as a function of time where the slope is less than a fourth predetermined threshold.

8. The method of claim 2, wherein determining the current drop time comprises calculating an inflection point in the measured current as a function of time.

9. The method of claim 1, wherein the correction factor comprises about zero when the fill time is less than a first fill time threshold.

10. The method of claim 1, wherein the correction factor is calculated in view of the fill time when the fill time is greater than a first fill time threshold and less than a second fill time threshold.

11. The method of claim 1, wherein the correction factor comprises a constant value when the fill time is greater than a second fill time threshold.

12. The method of claim 1, wherein the step of calculating the corrected analyte concentration when the first analyte concentration in the sample is less than a threshold value comprises calculating a sum of the correction factor and the first analyte concentration in the sample.

13. The method of claim 1, wherein the step of calculating the corrected analyte concentration in the sample when the first analyte concentration in the sample is greater than a threshold value comprises:
dividing the correction factor by one hundred and adding one to give an intermediate term; and
multiplying the intermediate term by the first analyte concentration to give a fill time corrected analyte concentration.

14. The method of claim 1, in which detecting the presence of the sample comprises: applying an electric potential between the two electrodes, and
measuring a change in current values that is greater than a fifth predetermined threshold.

15. The method of claim 1, in which detecting the presence of the sample comprises: applying an electric potential between the two electrodes, and
measuring a change in current values that is less than a sixth predetermined threshold.

16. The method of claim 1, in which detecting the presence of the sample comprises: applying a generally constant current between the two electrodes, and
measuring a change in an electric potential that is greater than a seventh predetermined threshold.

17. The method of claim 1, in which detecting the presence of the sample comprises: applying a generally constant current between the two electrodes, and
measuring a change in an electric potential that is less than an eighth predetermined threshold.

18. The method of claim 1, in which detecting the presence of the sample is performed by a microprocessor of an analyte measuring machine.

19. The method of claim 1, in which reacting of the analyte generates an electroactive species that is measured as a current by the two electrodes.

20. An electrochemical system, comprising:
(a) an electrochemical sensor including electrical contacts configured to mate with a test meter, the electrochemical sensor comprising:
(i) a first electrode and a second electrode in a spaced apart relationship, and
(ii) a reagent; and
(b) the test meter including a processor configured to determine a fill time of a sample, calculate a prepulse time using the determined fill time, receive current data from the electrochemical sensor upon application of a voltage to the electrochemical sensor for a period of time equal to the calculated prepulse time, and determine a corrected analyte concentration of a sample based on a calculated concentration of an analyte and a correction factor, the correction factor being based upon the determined fill time of the sample in the electrochemical sensor.

21. The electrochemical system of claim 20, wherein the test meter is configured to apply an electric potential between the two electrodes while the sample is introduced, the processor being configured to determine a current drop time based on the measurement of current as a function of time, the current drop time corresponding to the fill time of the sample in the sensor.

22. The electrochemical system of claim 20, wherein the test meter includes data storage containing an analyte concentration threshold, a first fill time threshold, and a second fill time threshold.

23. The electrochemical system of claim 20, further comprising a heating element configured to heat at least a portion of the electrochemical sensor.

24. The electrochemical system of claim 20, wherein the electrochemical sensor comprises a glucose sensor.

25. The electrochemical system of claim 20, wherein the electrochemical sensor comprises an immunosensor.

26. The electrochemical system of claim 20, wherein at least one of the electrochemical sensor, the test meter, and the processor are configured to measure a temperature of the sample.

27. The electrochemical system of claim 20, wherein the analyte comprises C-reactive protein.

28. The electrochemical system of claim 20, wherein the analyte comprises glucose.

29. The electrochemical system of claim 20, wherein the sample comprises blood.

30. The electrochemical system of claim 20, in which the first and second electrodes comprise at least one of an opposing faced orientation and a facing orientation.

* * * * *